(12) United States Patent
Miyake et al.

(10) Patent No.: US 7,495,760 B2
(45) Date of Patent: Feb. 24, 2009

(54) DEVICE AND METHOD FOR EVALUATING OPTICAL DISTORTION OF TRANSPARENT PLATE BODY

(75) Inventors: Atsushi Miyake, Minato-ku (JP); Yuki Yoshimura, Minato-ku (JP); Kunihiro Hiraoka, Kyoto (JP)

(73) Assignee: KDE Corporation, Osaka (JP)

( * ) Notice: Subject to any disclaimer, the term of this patent is extended or adjusted under 35 U.S.C. 154(b) by 244 days.

(21) Appl. No.: 10/540,785

(22) PCT Filed: Dec. 15, 2003

(86) PCT No.: PCT/JP03/16015

§ 371 (c)(1),
(2), (4) Date: Jun. 27, 2005

(87) PCT Pub. No.: WO2004/061437

PCT Pub. Date: Jul. 22, 2004

(65) Prior Publication Data
US 2006/0098190 A1    May 11, 2006

(30) Foreign Application Priority Data
Dec. 27, 2002 (JP) ............................ 2002-381004
Jun. 19, 2003 (JP) ............................ 2003-174927

(51) Int. Cl.
*G01N 21/00* (2006.01)
(52) U.S. Cl. .................................. 356/239.1
(58) Field of Classification Search .............. 356/239.1, 356/429–431, 605
See application file for complete search history.

(56) References Cited

U.S. PATENT DOCUMENTS 5,216,481 A * 6/1993 Minato ..................... 356/239.1
6,509,967 B1 * 1/2003 Pingel et al. ............. 356/239.1

FOREIGN PATENT DOCUMENTS

| JP | 2-73140 | 3/1990 |
| JP | 11-148813 | 6/1999 |
| JP | 2002-148195 | 5/2002 |

OTHER PUBLICATIONS

WO98/17993, pub: Apr. 30, 1998, Pingel et al.*

* cited by examiner

*Primary Examiner*—Tarifur Chowdhury
*Assistant Examiner*—Jonathon D Cook
(74) *Attorney, Agent, or Firm*—RatnerPrestia

(57) ABSTRACT

To provide estimating apparatus and method of the optical distortion of light transmitted through a transparent plate-shaped body.

Upon picking-up a grid pattern via a glass plate by an image pickup device, $4n\pm\alpha$ CCD pixels correspond to n grids (pair of a bright portion and a dark portion), thereby generating $\alpha$ moire fringes. Sine waves with a phase A and sine waves with a phase B deviated from the phase A by 90° are generated based on gray data of the picked-up image in this state. A phase angle at each pixel on the Lissajous figure is calculated based on the sine waves with the phases A and B, and the refractive power is calculated based on a phase angular speed, serving as the difference between the phase angles of the pixels.

8 Claims, 35 Drawing Sheets

IN CASE OF X=4 i = 0  
GROUP 1  
○ ○ ○ ○  
1  2  3  4 i = 1  
GROUP 2  
○ ○ ○ ○  
5  6  7  8 i = 2  
GROUP 3  
○ ○ ○ ○  
9  10  11  12

|  | $C_{4i+1}$ | $C_{4i+2}$ | $C_{4i+3}$ | $C_{4i+4}$ |
|---|---|---|---|---|
| FOR WAVE A | + | + | − | − |
| FOR WAVE B | + | − | − | + |
| FOR WAVE A | − | + | + | − |
| FOR WAVE B | + | + | − | − |

FIG. 17

FLOWCHART OF SOFTWARE PROCESSING h : NUMBER OF PIXELS PER PITCH
  fugo : SIGN FOR CALCULATING ORIGINAL IMAGE DATA
 shift : AMOUNT OF SHIFT FOR CALCULATION FOR GENERATING SINE WAVES SHIFTED AT 90°
  data : ORIGINAL IMAGE DATA
   aaa : DATA ON SINE WAVES WITH PHASE A
   bbb : DATA ON SINE WAVES WITH PHASE B
   ccc : PHASE ANGLE ON LISSAJOUS FIGURE
   ddd : ANGULAR SPEED
 pixel : NUMBER OF PIXELS FOR PROCESSING

STEP 1
  GENERATE SIGN

GENERATE ++++----++++----++++----

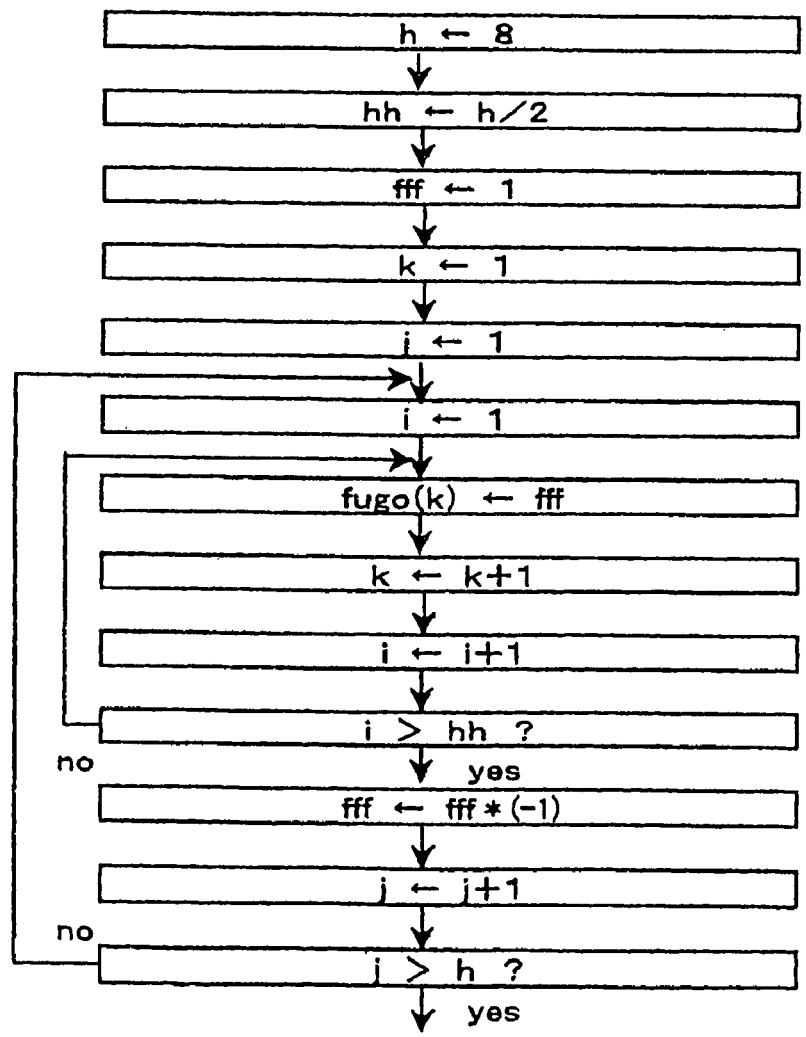

STEP 2 GENERATE SINE WAVES WITH PHASE A AND PHASE B

FIG. 24

FLOWCHART OF SOFTWARE PROCESSING
(PHASE A, PHASE B, PHASE C, PHASE D)

```
        h : NUMBER OF PIXELS PER PITCH
     fugo : SIGN FOR CALCULATING ORIGINAL IMAGE DATA
    shift : AMOUNT OF SHIFT FOR CALCULATION FOR GENERATING
            SINE WAVES SHIFTED AT 90°
     data : ORIGINAL IMAGE DATA
  phase_a : DATA ON SINE WAVES WITH PHASE A
  phase_b : DATA ON SINE WAVES WITH PHASE B
  phase_c : DATA ON SINE WAVES WITH PHASE C
  phase_d : DATA ON SINE WAVES WITH PHASE D
      ccc : PHASE ANGLE ON FIGURE
      ddd : ANGULAR SPEED
    pixel : NUMBER OF PIXELS FOR PROCESSING
STEP 1
   GENERATE SIGN
      GENERATE ++ —++ —++ —
```

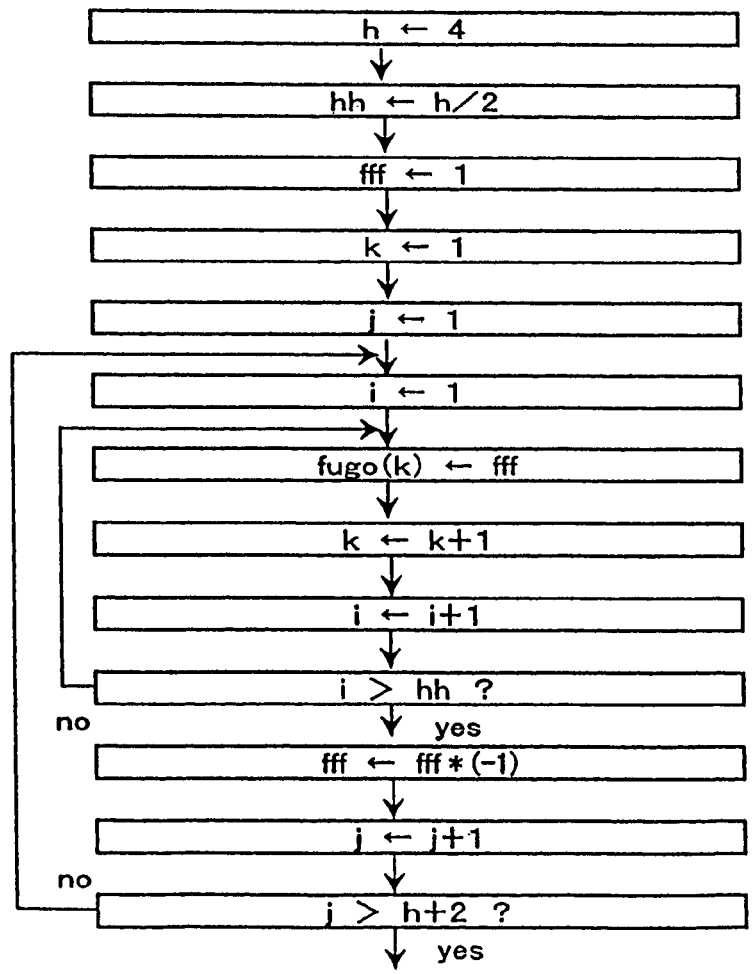

CONVEYING DIRECTION OF GLASS

DEVICE AND METHOD FOR EVALUATING OPTICAL DISTORTION OF TRANSPARENT PLATE BODY

CROSS-REFERENCE TO RELATED APPLICATIONS

This application is a 371 of International Application No. PCT/JP2003/016015 filed Dec. 15, 2003.

BACKGROUND OF THE INVENTION

1. Field of the Invention

The present invention relates to detecting and estimating apparatus and method of the optical distortion of transmitting light due to a defect existing on a transparent plate-shaped body, such as a glass plate, or the optical distortion of reflecting light due to the non-uniformity of surface smoothness of a glossy plate-shaped body.

2. Background Art

A defect on a transparent plate, e.g., a glass plate, includes a concave existing on the surface, a fallen foreign material serving as a defect formed by a foreign material fallen on the surface, a concave, like craters, existing at the mark of the fallen foreign material, and a foreign material and bubbles in the glass plate. Further, in the case of a glass plate covered with a transparent film on the surface, a defect of the transparent film includes a pinhole. These defects cause the optical distortion and, then, light is refracted by the optical distortion. Therefore, since the glass plate or the like with the optical distortion becomes a defective product, as an optical substrate, and is not used, it needs to be excluded by inspection.

In a method as disclosed in Japanese Patent Application Publication No. 8-220021, an image of a grid pattern is picked-up by a line sensor camera and the focal point is purposely out of the grid pattern, the difference between a bright portion and a dark portion does not exist to obtain a gray image, the refractive power of a transparent plate-shaped body changes the focal point, and the difference between the bright portion and the dark portion thus exists, thereby detecting a defect. However, in the method, the refractive power of the transparent plate-shaped body is not quantitatively measured on the basis of a unit of lens power (diopter).

On the contrary, in a method as disclosed in PCT Japanese Translation Patent Publication No. 2001-502799, in the case of picking-up an image of a grid pattern by a line sensor camera, the number of CCDs corresponding to the grids is just an integral multiple of the number of grids and the optical distortion is quantitatively detected. However, in order to accurately set the number of CCDs to an integral multiple, the method requires a grid with accurate pitch and width and a lens that does not change the width thereof on the grid pattern corresponding to a pixel at any position at a viewing angle of a telecentric lens.

Further, Japanese Patent Application Publication No. 4-98111 discloses a method for measuring the three-dimensional shape of a surface portion of the living body by fringe scan.

BRIEF SUMMARY OF THE INVENTION

The object of the present invention is to provide estimating apparatus and method of the optical distortion using the moire fringes generated by the interference between a grid pattern and a pixel for picking-up an image of the grid pattern, in which the detection with high precision is possible without requiring high nonuniformity of pitches and widths of grids in the image of the grid pattern.

Further, the another object of the present invention is to provide an estimating apparatus of the optical distortion using moire fringes generated by the interference between a grid pattern and a pixel for picking-up an image of the grid pattern with an inexpensive system structure.

Then, reference symbol X is equal to 4p (where reference symbol p is an integer of 1 or more), and $Xn\pm\alpha$ pixels correspond to n grids (pair of a bright portion and a dark portion) where reference symbols n and a denote integers of 1 or more.

Specifically, in the case of picking-up an image of grid patterns having the bright portions and the dark portions with a predetermined pitch and a predetermined width alternately repeated in one direction by using a line sensor camera having a plurality of pixel arrays in the same direction as the array direction of the grid patterns, $Xn\pm\alpha$ pixels correspond to n grids (pairs of the bright portion and the dark portion) included in the grid pattern. Here, a set of $Xn\pm\alpha/n$ pixels sequentially corresponds to each of the grids.

Further, in the case of picking-up an image of the grid patterns formed by alternately repeating the bright portions and the dark portions like a checker pattern by using a matrix camera when reference symbol Y is equal to 4p (where reference symbol p is an integer of 1 or more) and reference symbols m and β are integers of 1 or more, $Xn\pm\alpha$ pixels in the lateral direction of the matrix camera correspond to n grids (pairs of the bright portion and the dark portion) in the lateral direction included in the grid patterns, and $Ym\pm\beta$ pixels in the longitudinal direction of the matrix camera correspond to m grids (pairs of the bright portion and the dark portion) in the longitudinal direction included in the grid patterns. Here, a set of $X\pm\alpha/n$ pixels sequentially corresponds to the grid in the lateral direction, and a set of $Y\pm\beta/m$ pixels sequentially corresponds to the grid in the longitudinal direction.

Thus, with a corresponding relationship between the CCD pixels and the grids, in which α (or/and β) are deviated from an integral multiple of the number of grids, the amount of distortion is calculated, as the logic, thereby responding to the gradual change of the amount of deviation due to the variation in precision of the grid pattern or lens. Thus, the system is entirely structured with low costs.

Specifically, according to the present invention, there is provided an estimating apparatus of the amount of optical distortion of light transmitted through a transparent plate member with nonuniformity of refractive power of the transparent plate-shaped body, comprising means for irradiating a grid pattern having an array of a bright portion and a dark portion with a constant pitch and a constant width, means for picking-up the grid pattern by using an image pickup device, means for inputting a signal from the image pickup device, as gray image data, means for supporting and conveying the transparent plate-shaped body in an optical line ranging from the grid pattern to the image pickup device; and image processing means for processing the gray image data inputted from the image pickup device, wherein, upon picking-up the image of the grid pattern on the image pickup device, $Xn\pm\alpha$ CCD pixels correspond to n grids, thereby generating α moire fringes, and the image processing means comprises means for calculating a plurality of types of sine waves deviated in phase at 90° from image data of the moire fringes; means for obtaining a phase angle at each pixel based on the plurality of types of sine waves; and means for calculating refractive power of the optical distortion based on the difference in phase angles between the pixels.

According to the present invention, there is provided an estimating apparatus of the amount of optical distortion of light reflected to a glossy plate-shaped body with nonuniformity of surface smoothness of the plate-shaped body, comprising means for irradiating a grid pattern having an array of a bright portion and a dark portion with a constant pitch and a constant width means for picking-up a reflected image of the grid pattern by using an image pickup device, means for inputting a signal from the image pickup device as gray image data, means for supporting and conveying the glossy plate-shaped body so that light from the grid pattern is reflected to the plate-shaped body and is incident on the image pickup device; image processing means for processing the gray image data inputted from the image pickup device, wherein, upon picking-up the image of the grid pattern on the image pickup device, $Xn \pm \alpha$ CCD pixels correspond to n grids, thereby generating $\alpha$ moire fringes, and the image processing means comprises: means for calculating a plurality of types of sine waves deviated in phase at 90° from image data on the moire fringes, means for obtaining a phase angle at each pixel based on the plurality of types of sine waves, and means for calculating refractive power of the reflected light based on the difference in phase angles between the pixels.

According to the present invention, there is provided a detecting apparatus of a defect having the optical distortion of a transparent plate-shaped body, comprising means for irradiating a grid pattern having an array of a bright portion and a dark portion with a constant pitch and a constant width, means for picking-up the grid pattern by using an image pickup device means for inputting a signal from the image pickup device as gray image data, means for supporting and conveying the transparent plate-shaped body in an optical path ranging from the grid pattern to the image pickup device; and image processing means for processing the gray image data inputted from the image pickup device, wherein upon picking-up the grid pattern to the image pickup device $Xn \pm \alpha$ CCD pixels corresponds to n grids generating $\alpha$ moire fringes, and the image processing means comprises means for calculating a plurality of types sine waves deviated in phase at 90° from image data of the moire fringes; means for obtaining a phase angle at each pixel from the plurality of types of sine waves; and means for detecting the defect having the optical distortion based on the difference in phase angle between the pixels.

According to the present invention, there is provided a detecting apparatus of a defect having the optical distortion of a surface of a glossy plate-shaped body, comprising means for irradiating a grid pattern with an array of a bright portion and a dark portion with a constant pitch and a constant width means for picking-up a reflected image of the grid pattern by using an image pickup device means for inputting a signal from the image pickup device as gray image data means for supporting and conveying the plate-shaped body so that light from the grid pattern is reflected to the glossy plate-shaped body and is incident on the image pickup device and image pickup means for processing the gray image data inputted from the image pickup device, wherein upon picking-up the grid pattern to the image pickup device generating $\alpha$ moire fringes $Xn \pm \alpha$ CCD pixels corresponds to n grids generating $\alpha$ moire fringes, and the image processing means comprises means for calculating a plurality of types sine waves deviated in phase at 90° from image data of the moire fringes, means for obtaining a phase angle at each pixel from the plurality of types of sine waves; and means for detecting the defect having the optical distortion based on the difference in phase angle between the pixels.

Further, the invention of the apparatus is established as the invention of a method. Further, the invention described above is established as a program for allowing an estimating apparatus or a computer to realize a predetermined function or a recording medium for recording the program.

Incidentally, the means does not merely mean physical means in the specification but may include the case of realizing the function of the means by hardware, software, or combination of the hardware and software. Further, the function of one means may be realized by two or more hardware and software, or the combination of the hardware and software, or functions of two or more means may be realized by one hardware and software or the combination of the hardware and software.

BRIEF DESCRIPTION OF THE SEVERAL VIEWS OF THE DRAWINGS

FIG. 17 is a flowchart showing one sequence of image processing;

FIG. 24 is a flowchart showing one sequence of image processing;

DETAILED DESCRIPTION OF THE INVENTION

Hereinafter, a description is given of the first embodiment of the present invention will be described with reference to the drawings.

Figure 1:
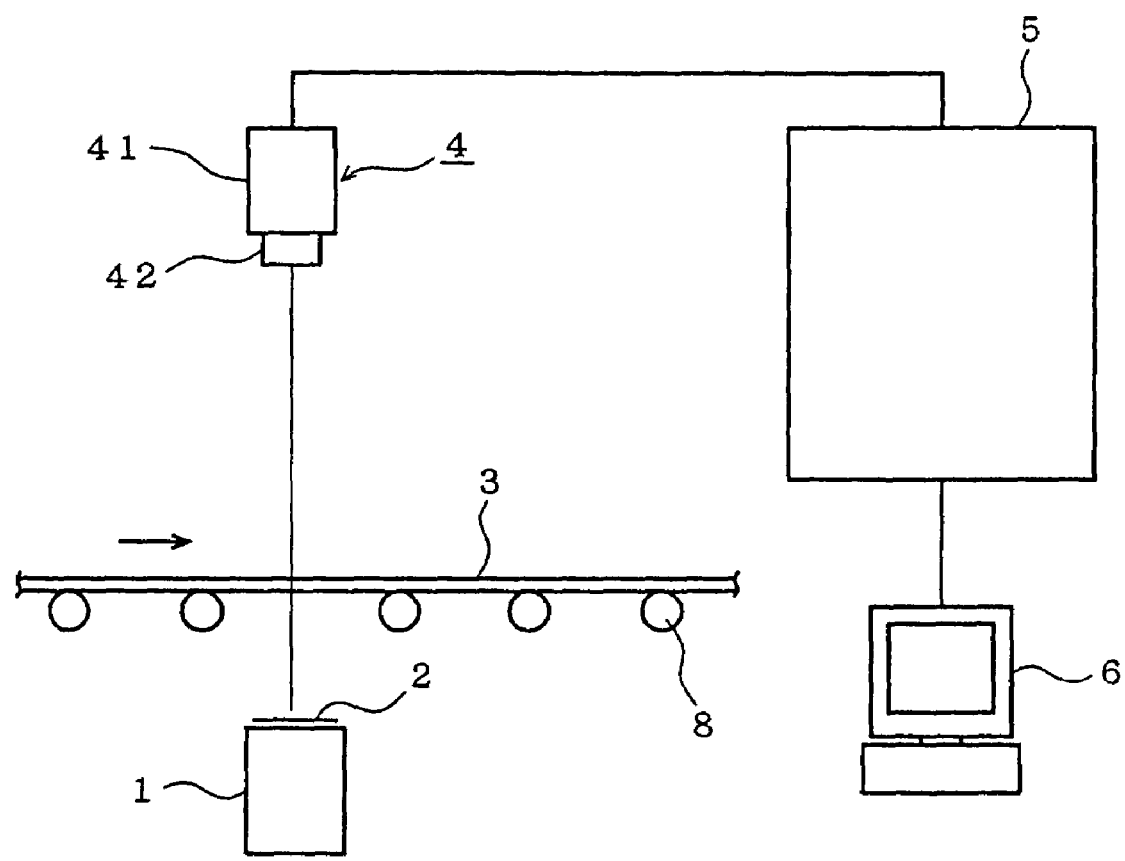
FIG. 1 is a diagram schematically showing the structure of one estimating apparatus according to the present invention.
Figure 2:
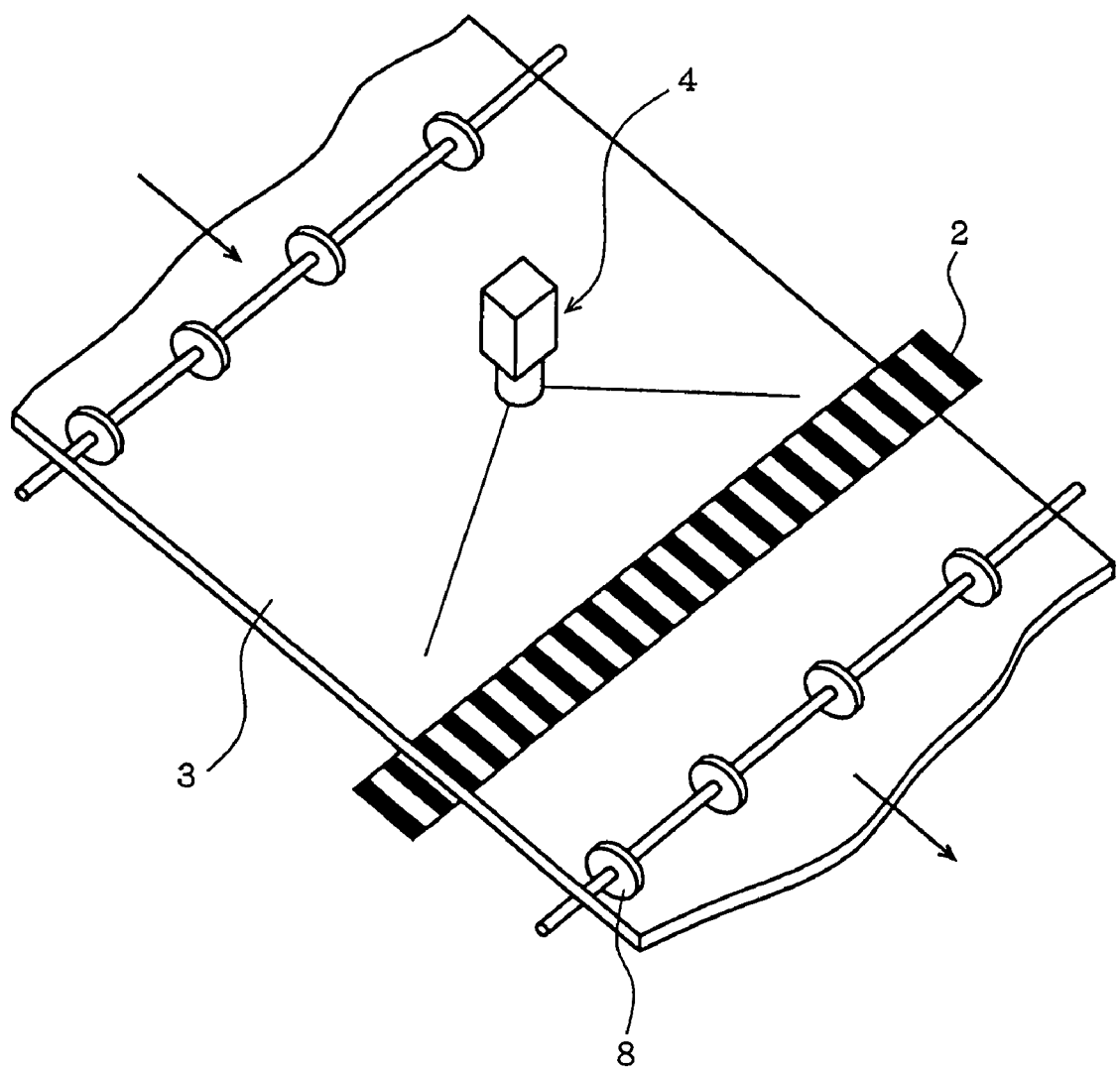
FIG. 2 is a perspective view showing the one estimating apparatus according to the present invention.

First, an estimating apparatus used for estimating the amount of optical distortion of light transmitted through a transparent plate-shaped body will be described. FIG. 1 is a diagram schematically showing the structure of one estimating apparatus according to the present invention. FIG. 2 is a perspective view showing the one estimating apparatus according to the present invention. Referring to FIGS. 1 and 2, the estimating apparatus comprises a grid pattern 2, image pickup means 4, image processing means 5, and display means 6. The grid pattern 2 is a grid formed by alternately repeating bright portions and dark portions with a predetermined pitch and a predetermined width in one direction. Incidentally, the grid pattern 2 may be structured by alternately forming a plurality of bright portions and dark portions like a checker pattern. The grid pattern 2 is a sheet-shaped or plate-shaped, and has a rectangular shape. In the example, the top surface of the grid pattern 2 is horizontally arranged.

The grid pattern 2 has a light source 1. The light source 1 uses, e.g., a fluorescent lamp. The light source 1 irradiates the grid pattern 2, with light, from the down direction. In addition to the fluorescent lamp, the light source may be a fiber illumination which uses a halogen lamp as a light source and guides light from the halogen lamp via fibers. Further, the light source may use an LED illumination which is a stick-shaped. The grid pattern may have an illumination. A plurality of bright portions and dark portions can alternately be formed by setting the same interval of illumination as the width of illumination with the arrangement of a large number of stripe illuminations.

Conveying means 8 (e.g. a roller) for conveying a transparent plate-shaped body 3, such as a glass plate of an inspection target, is arranged to the top of the grid pattern 2. In the example, as viewed on the plane, the grid pattern 2 and the conveying means 8 are arranged so that the conveying direction of the glass plate 3 is perpendicular to the array direction of the grid pattern 2.

The image pickup means 4 is a line sensor that repeats the one-dimensional scanning, and comprises a line sensor camera 41 using a CCD and a lens 42. The image pickup means 4 is arranged on the facing side of the light source 1 while sandwiching the conveyed transparent plate-shaped body 3. Further, the image pickup means 4 is attached to the top surface of the grid pattern 2 so that scanning lines of the line sensor camera is in parallel with the array direction of the grid patterns 2, and is arranged so as to capture the light transmitted through the grid patterns 2, serving as the field of view. The line sensor camera 41 comprises CCD pixels that are linearly arranged along the scanning lines. Since the field of view of the line sensor camera is determined, the number of the line sensor cameras may appropriately be determined in accordance with the width of the inspection target.

The conveying means 8 horizontally conveys the transparent plate-shaped body 3 between the above-described image pickup means 4 and the grid pattern 2. The inspection surface of the glass plate 3 is horizontal and is conveyed in the right direction as shown by an arrow in FIG. 1. The output of the image data with moire fringes from the line sensor camera 41 is inputted, as gray data, to the image processing means 5. The image processing means 5 calculates the sine waves with two types of phases A and B deviated in phase from the image data with moire fringes by an phase of 90°, obtains a phase angle of the pixel on the Lissajous figure based on the sine waves with the phases A and B, detects a defect having the optical distortion based on the difference in phase angles between the pixels, and calculates the amount of optical distortion.

The image processing means 5 may be, e.g., a computer. If the output of the line sensor is an analog signal, the signal needs to be converted into a digital signal and to be captured in the computer. Therefore, the image processing means 5 needs to further have an image input device having at least an analog/digital converting function. If the line sensor camera 41 is a digital camera, the analog/digital conversion is not necessary.

The display means 6 is realized by a display device, such as a CRT or a liquid crystal display. The display means 6 displays the output from the image processing means 5. Incidentally, the estimating apparatus detects the optical distortion of a defective grid in the array direction thereof.

In the above description, the image pickup means 4 and the grid pattern 2 are arranged in the vertical direction, and the inspection surface of the glass plate 3 is horizontally arranged. However, the arrangement of the components is not limited to this. FIGS. 3 to 7 show arrangement examples among the image pickup means, the grid pattern, and the inspection target.

Figure 3:
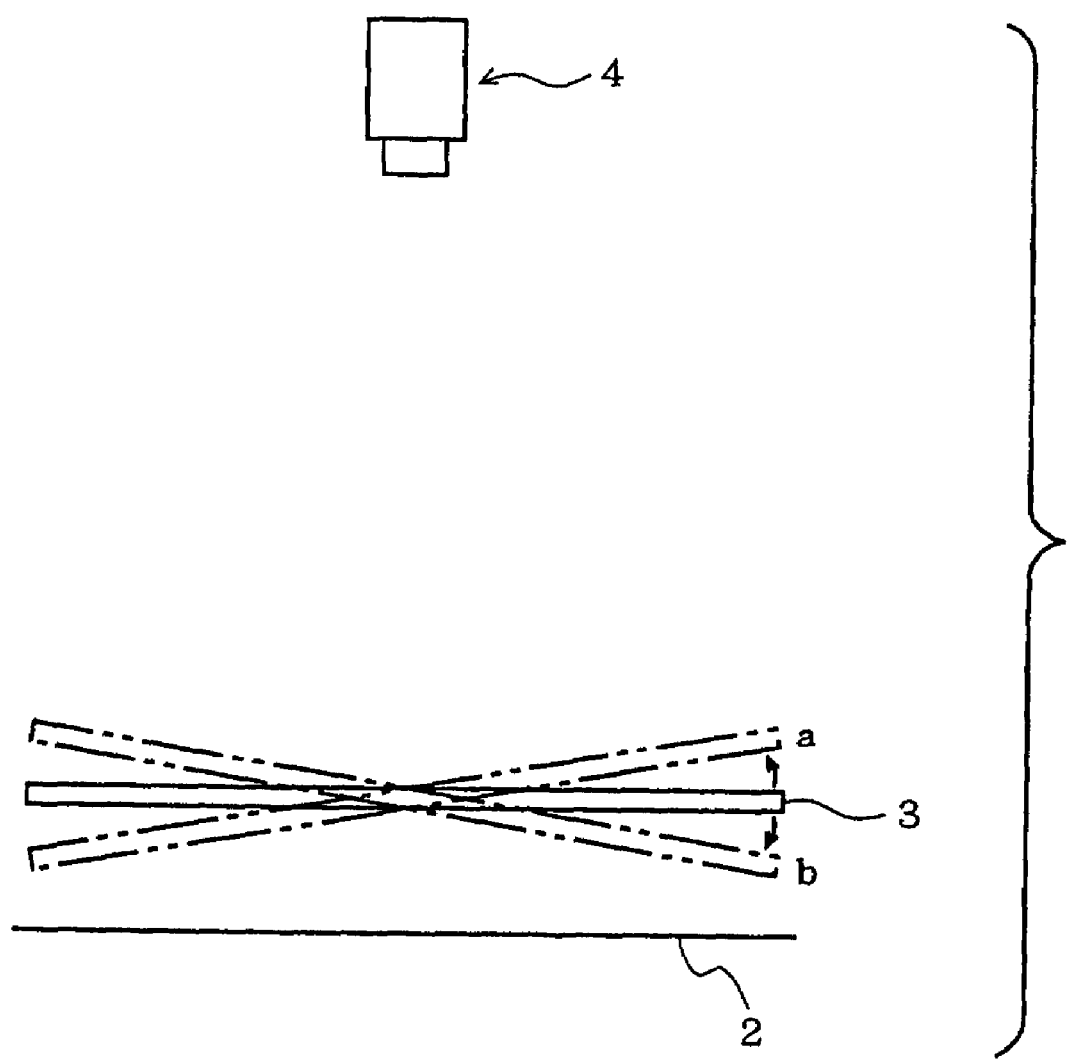
FIG. 3 is one end-view schematically showing the one estimating apparatus as viewed in the downstream of the conveying direction.
Figure 4:
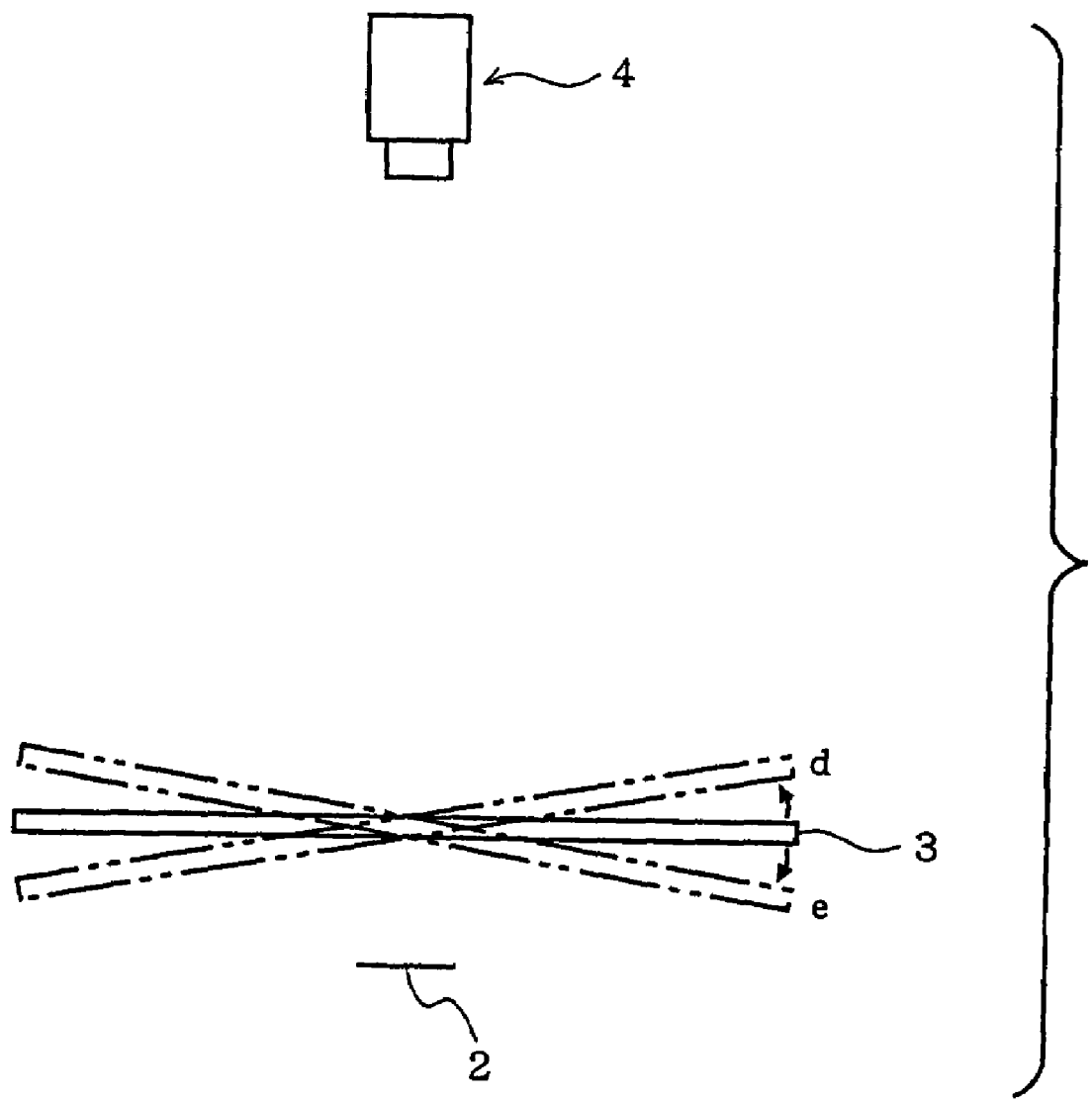
FIG. 4 is one side-view schematically showing the one estimating apparatus as viewed from the side of the conveying direction.
Figure 5:
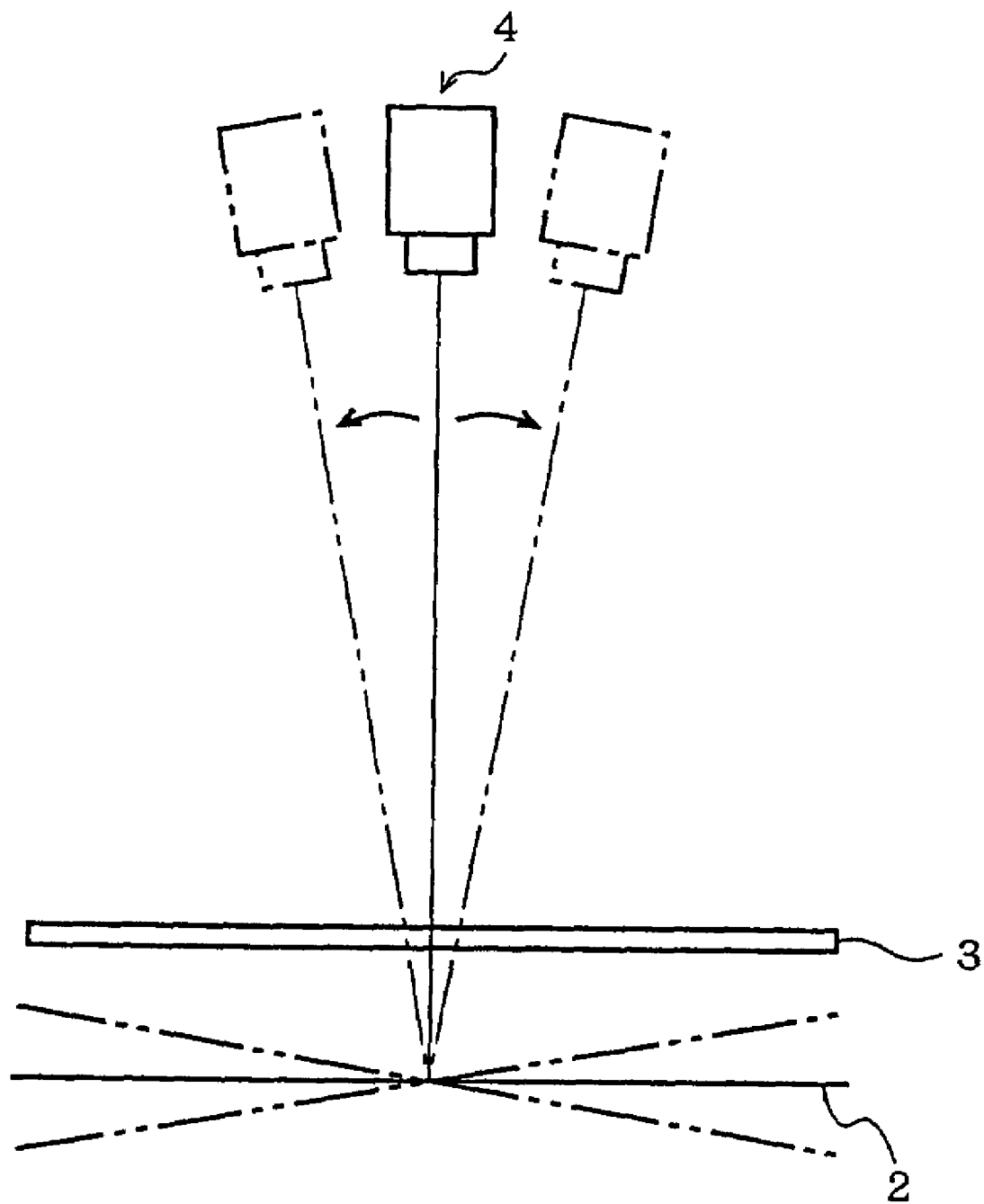
FIG. 5 is another end-view schematically showing the one estimating apparatus as viewed in the downstream of the conveying direction.
Figure 6:
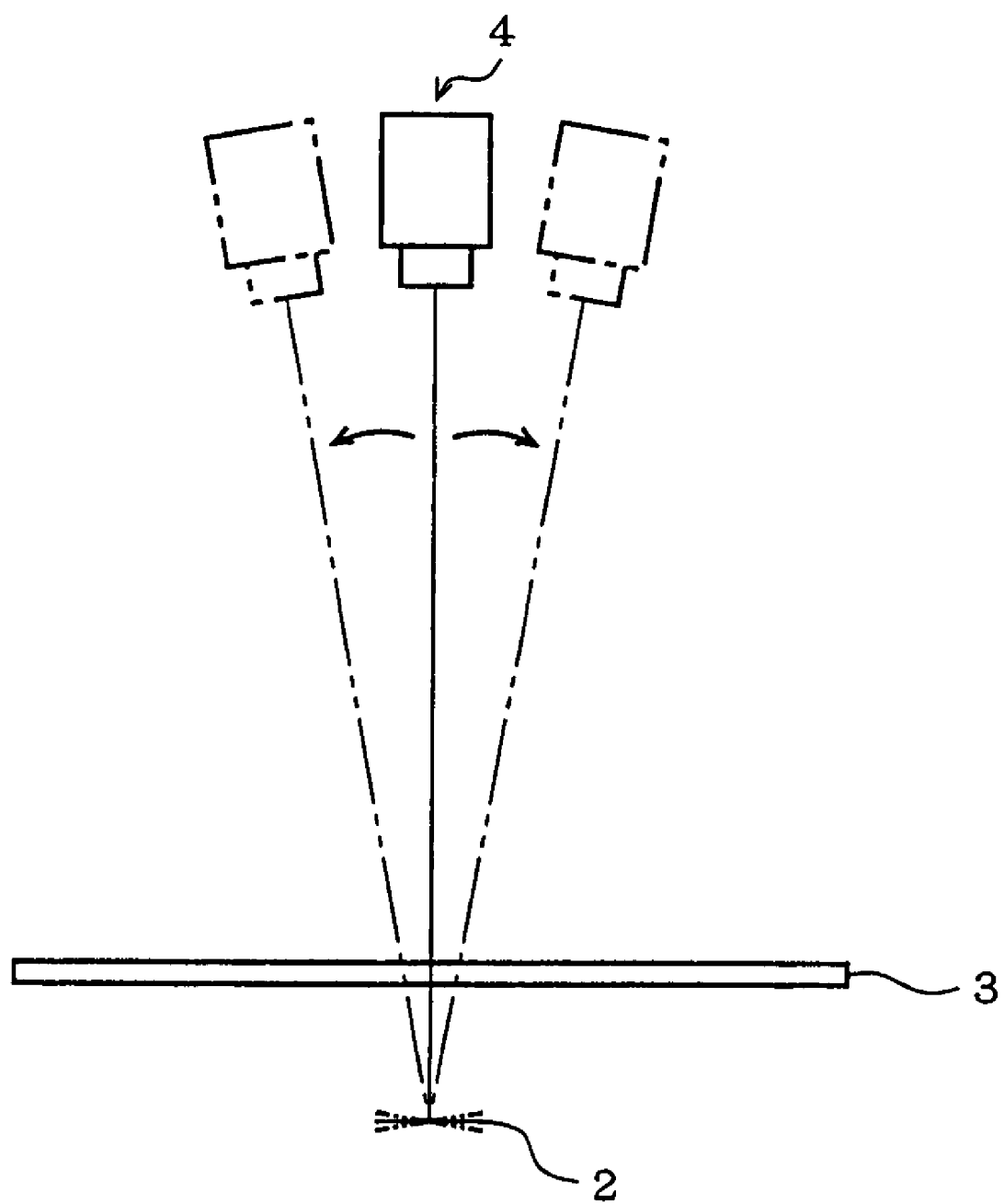
FIG. 6 is another side-view schematically showing the one estimating apparatus as viewed from the side of the conveying direction.
Figure 7A:
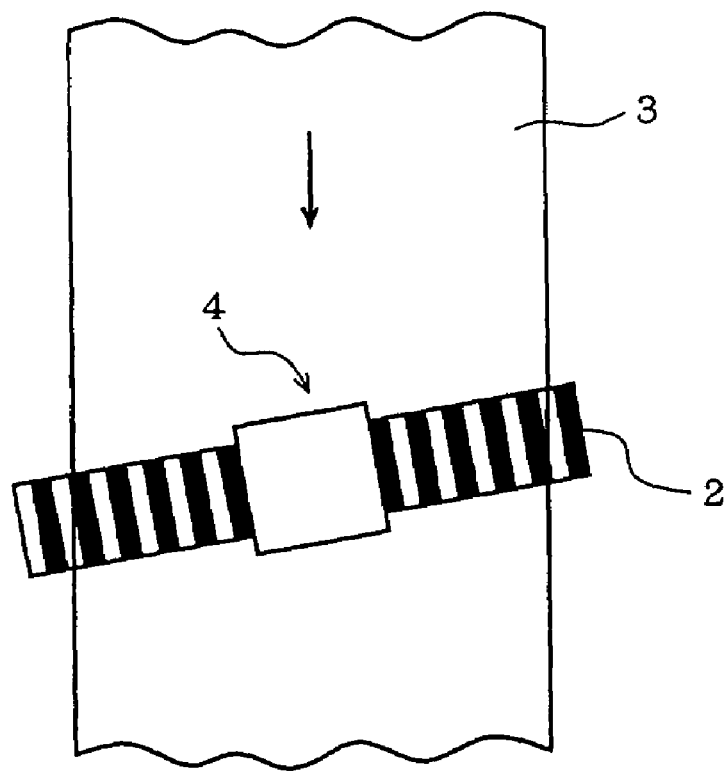
FIG. 7 is a plan view schematically showing the one estimating apparatus.
Figure 7B:
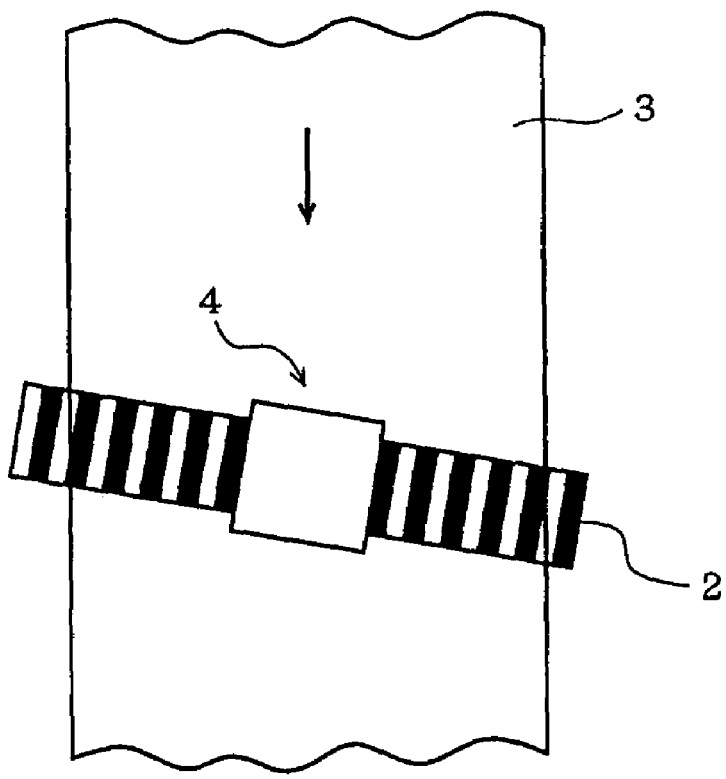

Here, FIGS. 3 and 5 are end views schematically showing the one estimating apparatus as viewed in the downstream of the conveying direction. FIGS. 4 and 6 are side views schematically showing the one estimating apparatus as viewed from the side of the conveying direction. FIG. 7 is a plan view schematically showing the one estimating apparatus.

As an arrangement example, the image pickup means 4 and the grid pattern 2 may be arranged in the vertical direction and the inspection surface of the glass plate 3 may be inclined from the horizontal direction. The inclination may be any of directions a and b shown in FIG. 3 or may be any of directions d and e shown in FIG. 4.

Since the positional relationship among the image pickup means 4, the grid pattern 2, and the glass plate 3 is relative, the inspection surface of the glass plate 3 may horizontally arranged and a line for connecting the image pickup means 4 and the grid pattern 2 may be inclined from the vertical direction, as shown in FIGS. 5 and 6.

In the above description, the conveying direction of the glass plate 3 is set, perpendicularly to the array direction of the grid pattern 2, as viewed on the plane. However, referring to FIG. 7, the conveying direction of the glass plate 3 diagonally crosses the array direction of the grid pattern 2, as viewed on the plane In the estimating apparatus shown in FIG. 1, the image pickup means 4 is arranged on the top side of the apparatus, and the image of the glass plate 3 is picked-up from the top. Or, the arranging direction of the image pickup means 4 can variously be changed.

For example, the image pickup means 4 may be arranged on the bottom of the apparatus, and the image of the glass plate 3 may be picked-up from the bottom. Specifically, the position of the image pickup means 4 shown in FIG. 1 may be exchanged with the positions of the grid pattern 2 and the light source 1, thereby realizing the light irradiation from the top and picking-up the image from the bottom.

Further, as another embodiment, the image pickup means 4 may be arranged to the side. For example, in the case of laterally conveying the glass plate 3 that stands-up or in the case of conveying the glass plate 3 longitudinally, e.g., in the down-draught direction, the surface of the inspection target of the glass plate 3 is in the lateral direction. Corresponding thereto, the image of the glass plate 3 may be picked-up from the side of the apparatus. If the image pickup means 4 is arranged to the side of the apparatus as described above, the grid pattern 2 and the light source 1 need to be arranged in the facing direction of the image pickup means 4.

Specifically, the image pickup means 4, the glass plate 3, the grid pattern 2, and the light source 1 shown in FIG. 1 may be rotated at a predetermined angle in the up/down direction with the rotational axis as center on the horizontal plane while keeping the relative position thereamong. The predetermined angle is 90° if the glass plate 3 vertically stands up.

The above-described arrangement examples shown in FIGS. 3 to 7 may be applied to both the embodiment in which the above-mentioned image pickup means 4 is arranged to the down side of the apparatus and the embodiment in which the image pickup means 4 is arranged to the side of the apparatus.

Figure 8:
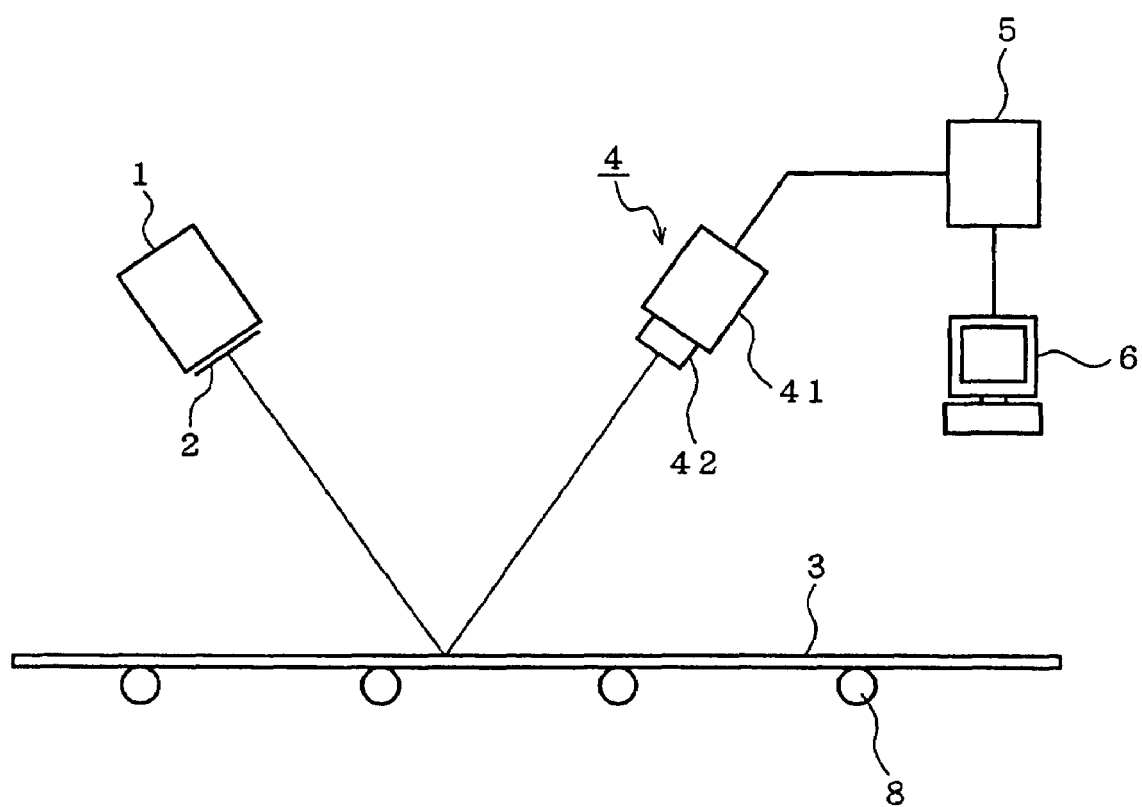
FIG. 8 is a diagram schematically showing the structure of another estimating apparatus according to the present invention.

Next, another example of structure of the estimating apparatus according to the present invention will be described. FIG. 8 is a diagram schematically showing the structure of the other estimating apparatus according to present invention. Common components shown in FIG. 8 to those shown in FIG. 1 are designated by the same reference symbols, and a detailed description thereof is omitted.

Referring to FIG. 8, an estimating apparatus is used for estimating the nonuniformity of the surface smoothness of a glossy plate-shaped body. Unlike the above-described estimating apparatus of the amount of optical distortion of light transmitted through the transparent plate-shaped body, the estimating apparatus has a positional relationship among the light source 1, the grid pattern 2, the plate member 3, the conveying means 8, and the image pickup means 4. The example sets a positional relationship, with which an image of the grid pattern 2 irradiated by the light source 1 is reflected to the plate member 3, and the image pickup means 4 picks-up the reflected image of the grid pattern 2.

(Correspondence Between the CCD Pixels and the Grids)

Figure 9:
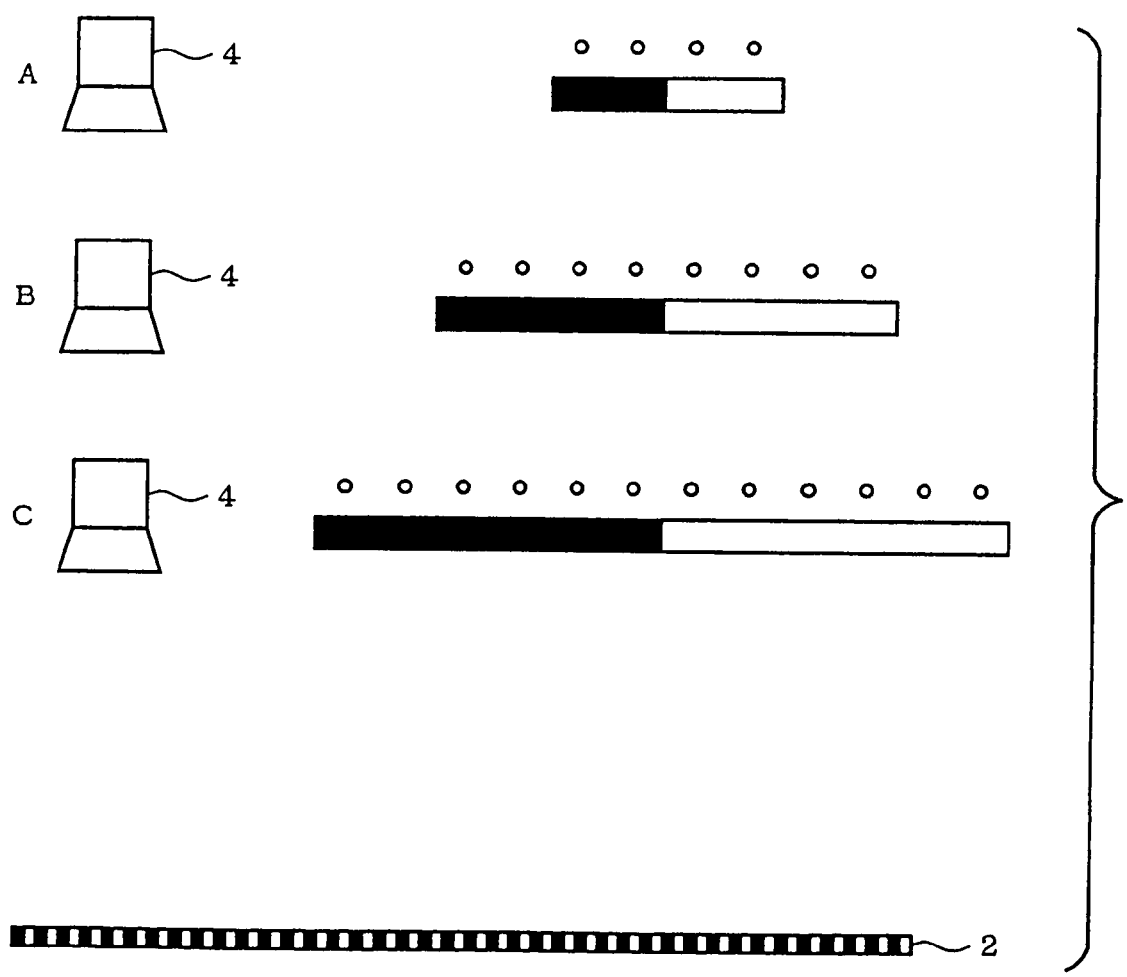
FIG. 9 is an explanatory diagram showing a corresponding relationship between a CCD pixel and a grid.

Next, a corresponding relationship between the CCD pixels and the grids, serving as one feature of the present invention will be described. Hereinafter, the corresponding relationship between the CCD pixels and the grids according to the present invention will be described by two steps for convenience's sake so as to easily describe it. FIG. 9 is an explanatory diagram showing the corresponding relationship between the CCD pixel and the grid.

(First Step)

First, according to the present invention, one set of a light-transmitting unit and a shielding unit is defined as one grid. Any one of grids included in the grid pattern 2 is selected and X CCD pixels correspond to the one grid. As a feature of the present invention, reference symbol X is an integral multiple of 4. Therefore, the number X is equal to 4p (where reference symbol p is an integer of 1 or more). According to the present invention, the light-transmitting unit and the shielding unit are based on the relative concept, the light-transmitting unit has a high light-transmittance, and the shielding unit has a transmittance lower than that of the light-transmitting unit. The light-transmitting unit and the shielding unit comprise a transparent glass portion and a black-lacquered glass portion.

The X CCD pixels correspond to one predetermined grid by adjusting the distance between the image pickup means 4 and the grid pattern 2. That is, the distance between the image pickup means 4 and the grid pattern 2 is reduced and, thus, the optical image of the grid is enlarged and the number of the CCD pixels corresponding to one grid is increased. On the contrary, the distance between the image pickup means 4 and the grid pattern 2 is increased and, thus, the number of the CCD pixels corresponding to one grid is reduced. The distance between the image pickup means 4 and the grid pattern 2 is adjusted as mentioned above, and a desired number X of the CCD pixels corresponds to one predetermined grid to determine a positional relationship therebetween.

A specific description is given with reference to FIG. 9. Referring to FIG. 9, a description is given on the assumption that the grid pattern 2 is fixed and the image pickup means 4 is movable in the facing direction of the grid pattern 2 (in the vertical direction in FIG. 9). First, one arbitrary grid is selected from the grid patterns 2, and a corresponding number of CCD pixels is determined on the basis of the grid. Preferably, the grid, serving as the reference, corresponds to a portion with high precision of width and pitch thereof. Referring to FIG. 9, when the image pickup means 4 is at the position shown by a reference symbol A in the drawing, four CCD pixels among the pixel array correspond to one grid, serving as the reference, in the grid pattern 2. The image pickup means 4 descends from this state and is close to the grid pattern 2 and, then, the number of CCDs corresponding to one grid is increased. The position of the image pickup means 4 is set at a position B where eight CCD pixels correspond to one grid. Thus, the eight CCD pixels correspond to one grid.

When twelve CCD pixels correspond to one grid, similarly, the image pickup means 4 further descends and a position C of the image pickup means 4 is set. Although the image pickup means 4 is movable and the grid pattern 2 is fixed in the drawing for convenience's sake, the present invention is not limited to this. The grid pattern 2 may be movable and the image pickup means 4 may be fixed, or both the grid pattern 2 and the image pickup means 4 may be movable. The above-described method is basically the same as that of the estimating apparatus shown in FIG. 8.

(Second Step)

As described above, the X CCD pixels correspond to one grid, thereby setting the distance between the image pickup means 4 and the grid pattern 2. However, the above-mentioned corresponding relationship between the grid and the CCD pixels becomes a non-matching one in many cases. The pitch between the grids forming the grid pattern 2 is minute. For example, the pitch between the grids is 90 μm in the light-transmitting unit and 90 μm in the shielding unit. In addition, the array pitch of CCD pixels is minute. Therefore, the number 4p of CCD pixels does not accurately correspond to the entire grids. Further, the precision of grid pattern may be problematic, and the pitch of the grid may be varied. Thus, a regular corresponding relationship between the grid and the pixels becomes a non-matching one. Even when the precision of grid pattern is high and the grid pattern is formed by plating a glass plate with chromium, the thermal expansion (due to the change in light source or air temperature) entirely or partly deviates the pitch of grid. In this case, the corresponding relationship between the grid and the pixel becomes a non-matching one.

As a consequence, when the regular corresponding relationship between the grid and the pixels is non-matching, a method for precisely detecting the defect of the transparent plate member is required. According to the present invention, when X CCD pixels correspond to one grid included in the grid pattern, the defect is detected even when a number ±α of CCD pixels is deviated from n continuous grids.

Next, a description is given of the deviation of the number ±α of CCD pixels from the n grids. FIG. 10 is a conceptual diagram for explaining the deviation of the CCD pixels from the grids. For convenience's sake of description, the number X is four and the number α is 1. Further, when four CCD pixels correspond to one grid, a description is given of the deviation of one CCD pixel for n continuous grids.

According to the present invention, as long as the n grids are included in the grid pattern, the n girds may be the entire grids or may be a part of grids. However, as conditions, the n grids included need to be continuous and corresponding CCD pixels need to be continuous. Further, a plurality of sets of n grids may exist in one grid pattern. That is, a plurality of deviated portions may exist in one grid pattern. Although sets of n grids is sequentially expressed as n1, n2, n3, ... n this case, the number of grids may be the same or be different.

Figure 10A:
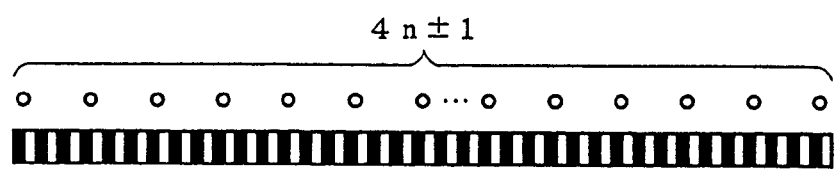
FIG. 10 is a conceptual diagram for explaining the deviation between the CCD pixel and the grid.

Referring to FIG. 10A, it is considered that the grid pattern comprises n grids. In this case, ±α pixels might be deviated in the entire grid patterns. In this deviation, if the number α is one then, a number 4n±1 of CCD pixels corresponds to the n grids in the entire grid patterns.

Figure 10B:
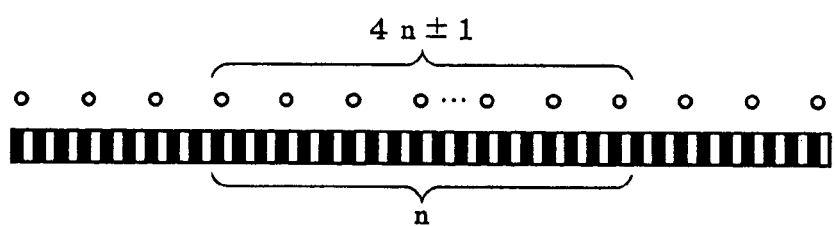
Figure 10C:
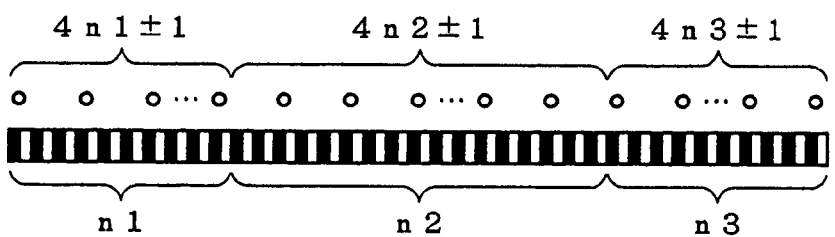

Referring to FIG. 10B, ±1 pixel may be deviated from the n continuous grids that partly form the grid patterns. In this case, 4n±1 CCD pixels correspond to the n grids that partly form the grid patterns. Further, one grid pattern may include a plurality of deviated portions. Specifically, referring to FIG. 10C, ±1 CCD pixel is deviated at the grids n1 to n3. Therefore, as shown in FIG. 10C, 4n1±1 CCD pixels correspond to n1 grids in a part of the grid patterns, 4n2±1 CCD pixels correspond to n2 grids in a part of the grid patterns, and 4n3±1 CCD pixels correspond to n3 grids in a part of the grid patterns. To the entire grid patterns, 4(n1+n2+n3)±3 CCD pixels correspond to (n1+n2+n3) grids.

With the above-mentioned corresponding relationship between the CCD pixels and the grids (corresponding relationship between n grids and Xn±α pixels), according to the present inventor, the present inventor confirms that the moire fringes are generated when the output of the line sensor camera is indicated as one-dimensional gray data. Further, under a consideration of the present inventor, it is confirmed that one peak of moire appears each time when one CCD pixel is deviated (α=1).

Figure 11:
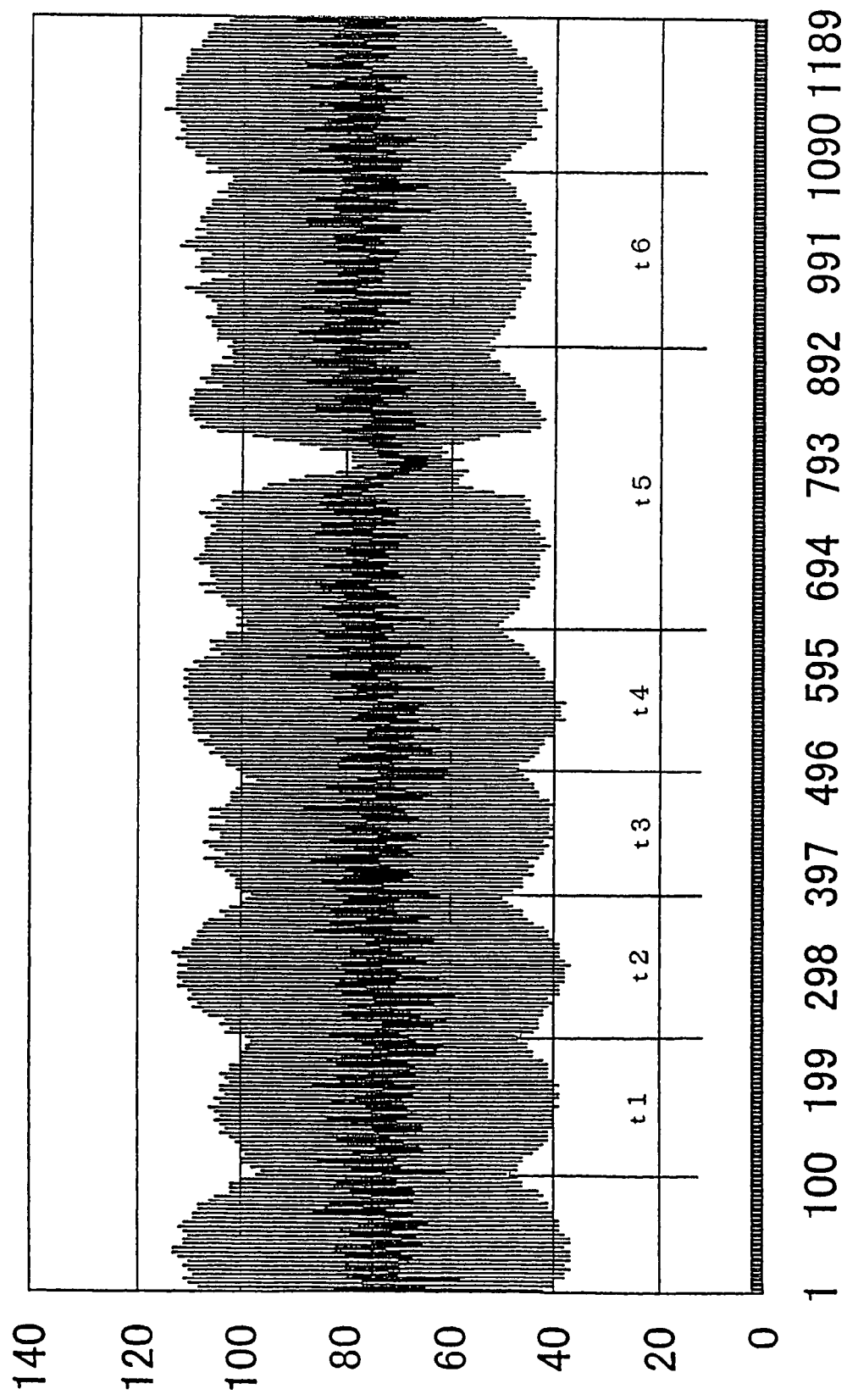
FIG. 11 is a graph indicating a portion corresponding to 1 to 1200 pixels of gray image data, as an output, upon picking-up an image of a grid pattern by a line sensor camera with 5000 pixels.

Referring to FIG. 11, 1 to 1200 pixels are indicated from gray image data as an output upon picking-up the image of the grid pattern by a line sensor camera with 5000 pixels. The X axis of graph denotes a length direction of grid patterns, and the Y axis denotes the strength of light. As will be understood with reference to the graph, a plurality of moire fringes are generated (at an interval tn in the drawing). As described above, one moire peak appears each time when one CCD pixel is deviated. Therefore, each peak indicates that one CCD pixel is deviated at the grid interval corresponding to the peaks. Specifically, a first grid-interval t1 includes 32 grids, and 4n−1=127 pixels correspond to the grids. Similarly, 135 pixels correspond to a grid interval t2 (34 grids), 123 pixels correspond to a grid interval t3 (31 grids), and 143 pixels correspond to a grid interval t4 (36 grids). Further, at a grid interval t5, two CCD pixels are deviated, thereby generating two peaks. The number of grids at the grid interval t5 is 66, and the corresponding number of pixels is 4n−2=262.

As described above, the position for generating the moire fringes on the gray data and the width of moire fringes depend on the deviation between the grids and the CCD pixels. Specifically, it depends on at which grid position the deviation is caused and for which number of grids on the deviation of one CCD pixel is generated. Therefore, the position for generating the moire fringes on the gray data and the width of moire fringes vary depending on the precision of grid pattern and the state of thermal expansion. That is, the grid pattern and the environmental temperature are varied, thereby changing the position, width, and number of moire fringes. According to the present invention, when a regular corresponding relationship between the CCD pixels and the grid is a non-matching one and the deviation is various, that is, is not constant, it is characterized that the chipped portion included in the glass plate is detected.

In the above description, it is considered that the deviation between the CCD pixel and the grid is caused due to the level of precision of grid patterns and the thermal expansion. However, according to the present invention, the deviation can purposely be caused. For example, Xn±α CCD pixels may purposely correspond to of entire grid pattern consisting of n grids. Or, Xn±α CCD pixels may purposely correspond to n grids which is n part of a grid pattern. As an example, when the total number of grids is 1000, 4000+1 CCD pixels may correspond to the entire 1000 grids and one moire fringe maybe generated. Further, 160+1 CCD pixels may correspond to 40 grids as a part and one moire fringe may be generated. Further, when the deviation is purposely caused and the deviation due to the thermal expansion simultaneously exists, a plurality of moire peaks due to the deviations might be generated. The present invention can be applied to this case.

The above-described purposed deviation has the following advantages. That is, in the first step described above even when X CCD pixels correspond to on predetermined grid, some degree of deviation is allowed without strict matching of the corresponding relationship therebetween. In the case of picking-up the grid pattern having minute pitches by the CCD pixels having an array of an excessively minute pitch, the accurate adjustment to correspond X CCD pixels to the grid is difficult, and the time and costs increase. Therefore, the allowance of the above-described deviation is excessively advantageous.

As described above, according to the present invention, when the output of CCD pixel is gray image data, the state of generating 1 or more moire fringes is obtained. The state is obtained by the correspondence of $Xn \pm \alpha$ CCD pixels to n continuous grids among the grid pattern. For example, as a method for generating the moire fringes, the image pickup means matches the grid pattern in the positional relationship near the corresponding position of X CCD pixels to one grid, and the image pickup means is vertically finely adjusted while viewing the gray data image from it, thereby generating desired moire fringes. According to the present invention, the deviation corresponding to $\alpha$ pixels to n girds is allowed. The thermal expansion of grid pattern may cause the above-described deviation, or the deviation may purposely be generated by adjusting the positional relationships between the image pickup means and the grid pattern. Therefore, the positioning of the image pickup means (or/and grid pattern) is easy without high precision. Since the measurement device does not require strict precision, the costs of device reduce.

According to the present invention, the number $\alpha$ ($\alpha$ of $Xn \pm \alpha$), serving as the deviation, is an integer of 1 or more. Preferably, the upper limit of $\alpha$ satisfies a relation of ($\alpha \leq n/10$). Because necessary moire fringes might not be generated when $\alpha$ is over the upper limit.

(Detection of the Chipped Portion)

Next, a description is given of a method for detecting the chipped portion based on the output of CCD pixel in which the moire is generated as mentioned above. As one feature according to the present invention, sine waves A and sine waves B deviated in phase from the sine waves A by 90° are calculated based on the output of CCD pixel in which the moire is generated.

Figures 12, 13:
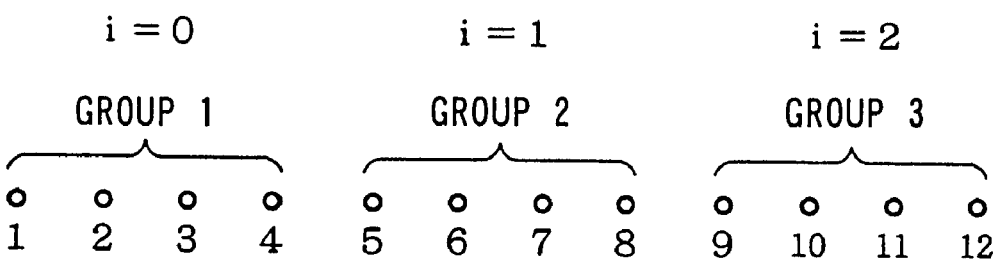
FIG. 12 is a conceptual diagram for explaining one assignment of reference symbols.
FIG. 13 is a conceptual diagram for explaining another assignment of reference symbols.

Specifically, there is provided a method for calculating the sine waves A and B by the output of CCD in the state in which an equation of X=4 is established, that is, $4n \pm \alpha$ CCD pixels correspond to n grids. Hereinbelow, a detailed description is given of the method for obtaining the sine waves A and B in the case of X=4. FIGS. 12 and 13 are conceptual diagrams for explaining the assignment of reference symbols.

(Step 1)

In the case of calculating the sine waves A and B, the positive or negative sign is assigned to an output (Cn) of the CCD pixel under a predetermined rule. Specifically, all pixels are divided into continuous groups having four continuous pixels. Then, the pixels in the group are designated by $C4i+1$, $C4i+2$, $Ci+3$, and $C4i+4$ ($0 \leq i$). Referring to FIG. 12, a description is given with 12 pixels. A first group of four pixels is designated by a group 1, a second group of four pixels is designated by a group 2, and a third group of four pixels is designated by a group 3. When the pixel further exists, the groups are designated by groups 4, 5, 6, . . . . For the group 1, the variable i is equal to 0 and, therefore, the pixels in the group 1 are designated by C1, C2, C3, and C4. Similarly, for the group 2, the variable i is equal to 1. For the group 3, the variable i is equal to 2 and, subsequently, the variable i increases one by one.

Next, reference symbols of a trigonometric function as shown in the following table is multiplied to four pixels included in the group by the sequential pattern. Specifically, reference symbol sin denotes the sine waves A, and reference symbol cos denotes the sine waves B. Because the sine waves B are deviated from the sine waves A at an angle of 90° and sin B is equal to cos A. Importantly in Table, the sequential pattern of the signs of cos shifts, by one sign, from the sequential pattern of the signs of sin. The signs in a column I does not necessarily correspond to the first pixel. Any sign after a column II may be a starting point.

TABLE 1

|  |  | Quadrant | | | |
| --- | --- | --- | --- | --- | --- |
|  |  | I | II | III | IV |
| Function | sin | + | + | − | − |
|  | cos | + | − | − | + |

For example, in order to obtain the sine waves A, referring to FIG. 13, (+, +, −, −) or (−, +, +, −) may be multiplied to the pixels in the group. However, in order to obtain the sine waves B, since the sequential pattern of the signs needs to shift by one sign. In the former case, (+, −, −, +) needs to be multiplied to the pixels in the group. In the latter case, (+, +, −, −) needs to be multiplied. As shown by the variable i in FIG. 13, the ± signs need to be multiplied to the pixels included in any group by the same sequential pattern.

More specifically, the sequential pattern of four ± signs multiplied to the four pixels in one group is under the following condition. First, the ± signs may sequentially be repeated in order of +, +, −, and −. Therefore, the sign multiplied to the first pixel in the group may be any of + and −. If the sign of the first pixel is +, for example, the sequential pattern may be any of a sequential pattern (+, +, −, −) and a sequential pattern (+, −, −, +). On the other hand, if the sign of the first pixel is −, the sequential pattern may be any of a sequential pattern (−, −, +, +) and a sequential pattern (−, +, +, −). Secondly, in order to obtain the sine waves B, the sequential pattern shifted from the sine waves A at 90°, that is, by one of the ± signs, is obtained. If the ± signs of the sine waves A is (−, +, +, −),for example, the ± signs of the sine waves B is (+, +, −, −) or (−, −, +, +). As mentioned above, the + or − sign is multiplied to the entire pixel output values under the above-described rule to obtain two types of pixel output values (Ck) with the sign for waves A and B. Sign assigning means of the image processing means 5 can perform processing for calculating the two types of pixel output value with the sign for waves A and B.

(Step 2)

Next, the sine waves A and the sine waves B are calculated. The sine waves A and B are obtained above with the two types of pixel output values with the sign for waves A and B by the following expression. Incidentally, sine-wave generating means of the image processing means 5 can perform the calculating processing of the sine waves A and sine waves B.

The sine waves A are obtained, with the pixel output value with the sign for waves A, by the following expression.

$$An = \sum_{k=n}^{n+3} ACk \quad \text{(Expression 1)}$$

(where reference symbol An denotes a phase A and reference symbol ACk denotes the pixel output value with the sign of a k-th pixel).

Next, the sine waves B are obtained, with the pixel output value with the sign for waves B, by the following expression.

$$Bn = \sum_{k=n}^{n+3} BCk \quad \text{(Expression 2)}$$

(where reference symbol Bn denotes a phase B and reference symbol BCk denotes the pixel output value with the sign of a k-th pixel).

Further, in the case of X=4, the following expressions denote the above-described processing for assigning the signs by using grouping and obtaining the A phase and the B phase.

i=integer of 0 or more.

$A4i+1=-C4i+1+C4i+2+C4i+3-C4i+4$ $A4i+2=+C4i+2+C4i+3-C4i+4-C4i+5$ $A4i+3=+C4i+3-C4i+4-C4i+5+C4i+6$ $A4i+4=-C4i+4-C4i+5+C4i+6+C4i+7$ $B4i+1=+C4i+1+C4i+2-C4i+3-C4i+4$ $B4i+2=+C4i+2-C4i+3-C4i+4+C4i+5$ $B4i+3=-C4i+3-C4i+4+C4i+5+C4i+6$ $B4i+4=-C4i+4+C4i+5+C4i+6-C4i+7$ (Expression 3)

Next, the phase angles at the pixels are obtained based on the above-obtained sine waves with the phases A and B. When reference symbol Hi denotes the phase angle at the pixel, the phase angle is obtained by an equation of Hi=ATAN(Bi/Ai). Phase angle calculating means of the image processing means 5 can perform the above-described processing for calculating the phase angle.

Figure 14:
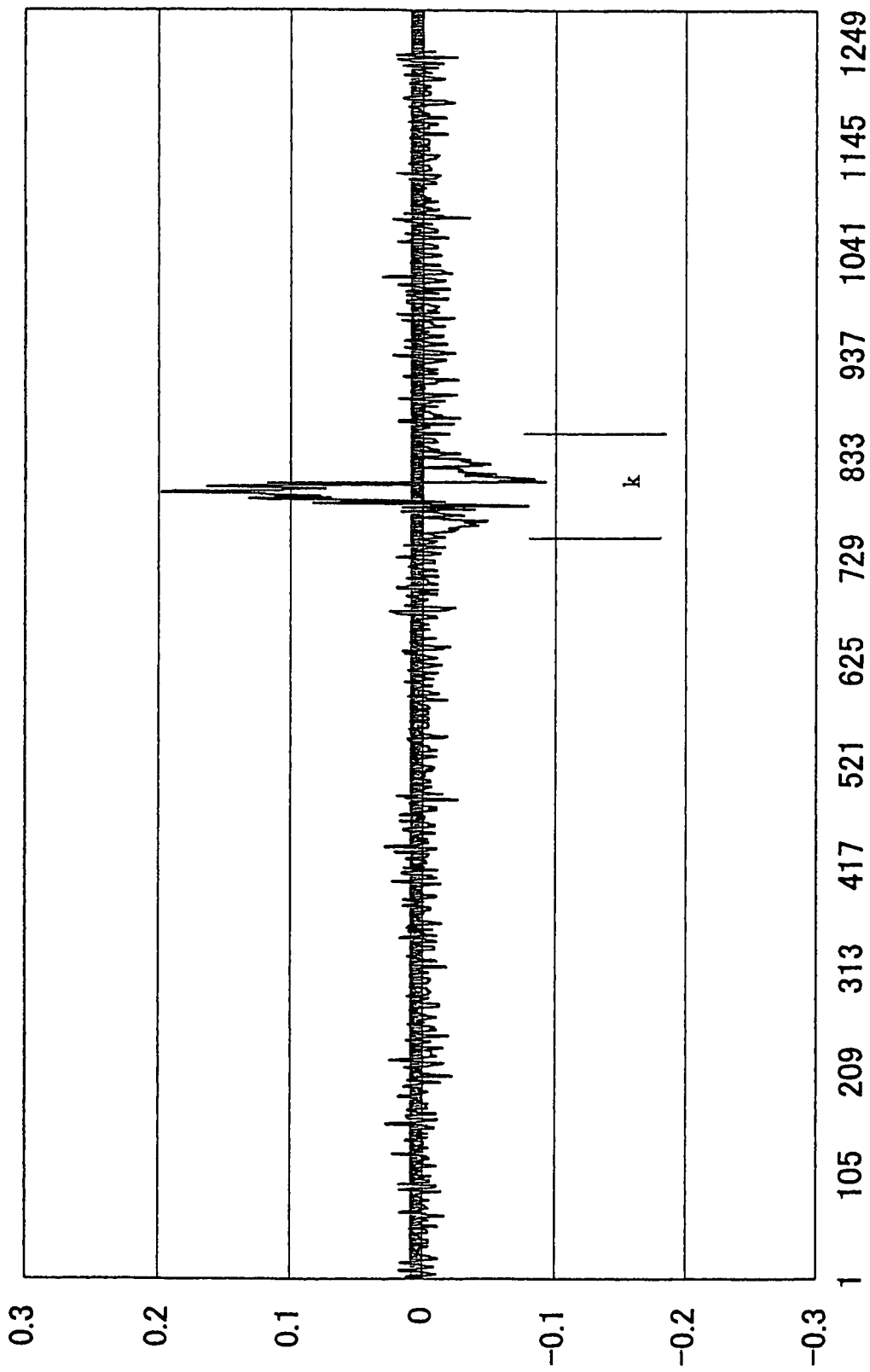
FIG. 14 is a diagram showing an example of a graph for a phase angular speed.

Next, the rate of change of phase angle, that is, the phase angular speed is obtained per pixel based on the phase angle of the pixel obtained as described above. Specifically, the phase angular speed is obtained by obtaining the difference in phase angles between the adjacent pixels. Reference symbol Di denotes the phase angular speed and the phase angular speed is then obtained by an equation of Di=Hi+1−Hi. FIG. 14 shows an example of a graph of the phase angular speed obtained as described above. Angular speed calculating means of the image processing means 5 can perform the above-described processing for calculating the phase angular speed.

FIG. 14 will be described. If the transparent plate-shaped body, serving as a measurement target, does not include the defect, it is confirmed that the phase angular speed Di is constant near 0. On the contrary, if the transparent plate-shaped body includes the defect, it is confirmed that the phase angular speed Di is a large value. Referring to FIG. 14, at an interval at which the transparent plate-shaped body does not include the defect, the phase angular speed is approximately 0. As will clearly be understood, the transparent plate-shaped body near an interval k includes the defect and the phase angular speed sharply changes.

In order to detect the defect with the distortion based on the calculating result of the phase angular speed, preferably, a constant threshold is set, for determination, to the value of the phase angular speed. That is, to the plate angular speed over the threshold, it is identified that the defect exists at the portion of the transparent plate-shaped body corresponding to the pixel of the portion. The threshold is arbitrarily set in accordance with the quality of the obtained transparent plate-shaped body. Specifically, if the quality is low, the threshold is set to be high. If not so, the threshold is set to be low. As described above, defect detecting means of the image processing means 5 can perform the processing for determining the phase angular speed over the preset threshold and detecting the defect of the transparent plate-shaped body corresponding to the pixel of the portion.

As a result, if a regular correspondence between the grid and the CCD pixels is deviated, it is possible to detect the defect included in the transparent plate-shaped body, as the measurement target, with high precision.

(Calculation of Refractive Power)

Next, a method for obtaining the refractive power of the transparent plate-shaped body corresponding to the pixel will be described based on the obtained phase angular speed.

First, at the above obtained phase angular speed, the moire fringes are generated due to the deviation in pitch between the grid and the CCD pixel, and the phase angular speed Di is shifted from 0, by the angular speed of the phase angles corresponding to the deviation. Therefore, preferably, all phase angular speeds Di are averaged, thereby correcting the amount of deviation and setting it to 0.

Specifically, a correcting method will be described. First, all the phase angular speeds Di are averaged. Reference symbol M denotes the total number of pixels reference symbol AVE denotes the average thereof. Then, the average of all the phase angular speeds Di is obtained by an equation of AVE=ΣDi/M. When reference symbol Ei denotes the phase angular speed after correction, the phase angular speed after correction is obtained by an equation of:

$Ei=Di-AVE$.

Correcting means of the image processing means 5 can perform the above-described processing.

Next, the refractive power of the transparent plate-shaped body is obtained per pixel based on the above-described phase angular speed Ei after correction.

A specific description is given. First, the followings are set.
LP: Refractive power (unit: dpt (diopter))
f: Focusing distance
P: Pitch of grid
L: Length between glass and grid
θ: Refractive angle due to glass Amount of deviation by one pixel at an i-th pixel=(Ei/2π)×P Angle of deviation by one pixel at the i-th pixel:
θi=tan θi=(Ei/2π)×P×(1/L)
(Because θi is small), a relation between the pitch corresponding to one pixel: G=P/4 and the focusing distance fi for lens operation at the portion is tan θi=G/fi.

Therefore, reference symbol LPi denotes the refractive power at the i-th pixel and then is expressed as follows.

$LPi=1/fi=(\tan \theta i)/G=(Ei/2\pi)\times P\times(1/L)\times(4/P)=2Ei/(\pi\times L)$ (dpt)

The refractive power LPi is multiplied by 1000, thereby obtaining a unit of mdpt.

In the above-described method, the refractive power at the pixel is obtained. Further, the refractive power of the portion of the transparent plate-shaped body corresponding to the pixel is obtained. Therefore, if the regular correspondence between the grid and the CCD pixel includes the deviation, it is possible to calculate the refractive power at the desired portion of the transparent plate-shaped body, as the measurement target. Refractive-power calculating means of the image processing means 5 can perform the calculation of refractive power.

Next, an integrated value of the amount of deviation (angle at the phase) at the pixel is obtained. The phase angular speed Ei is integrated, thereby obtaining the amount of integration for deviation of the phase angle at the pixel.

Specifically, the amount of integration for deviation is obtained by

F1=0
Fi+1=Fi+Ei.

Deviation integrating means of the image processing means 5 can perform the above-described integration of the amount of deviations.

Further, a light bending angle is obtained at the pixel based on the amount Fi of integration of deviations. In the above-described method, if the regular correspondence between the grid and CCD pixel includes the deviation, the amount of integration of deviations at the pixel is obtained, thereby obtaining the light bending angle at the pixel.

First Embodiment

Figure 15:
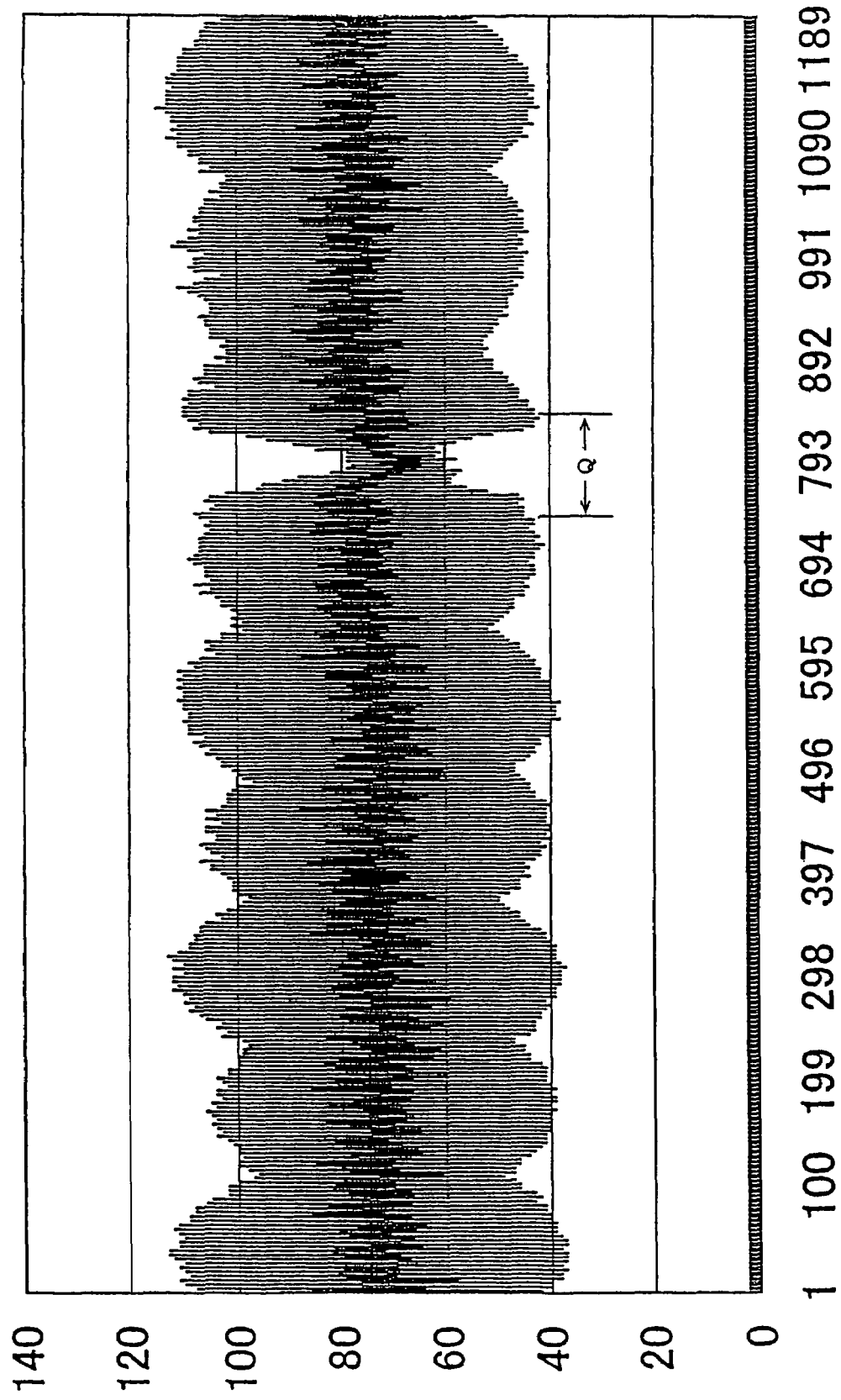
FIG. 15 is a diagram showing an example of a graph of gray data.
Figure 16:
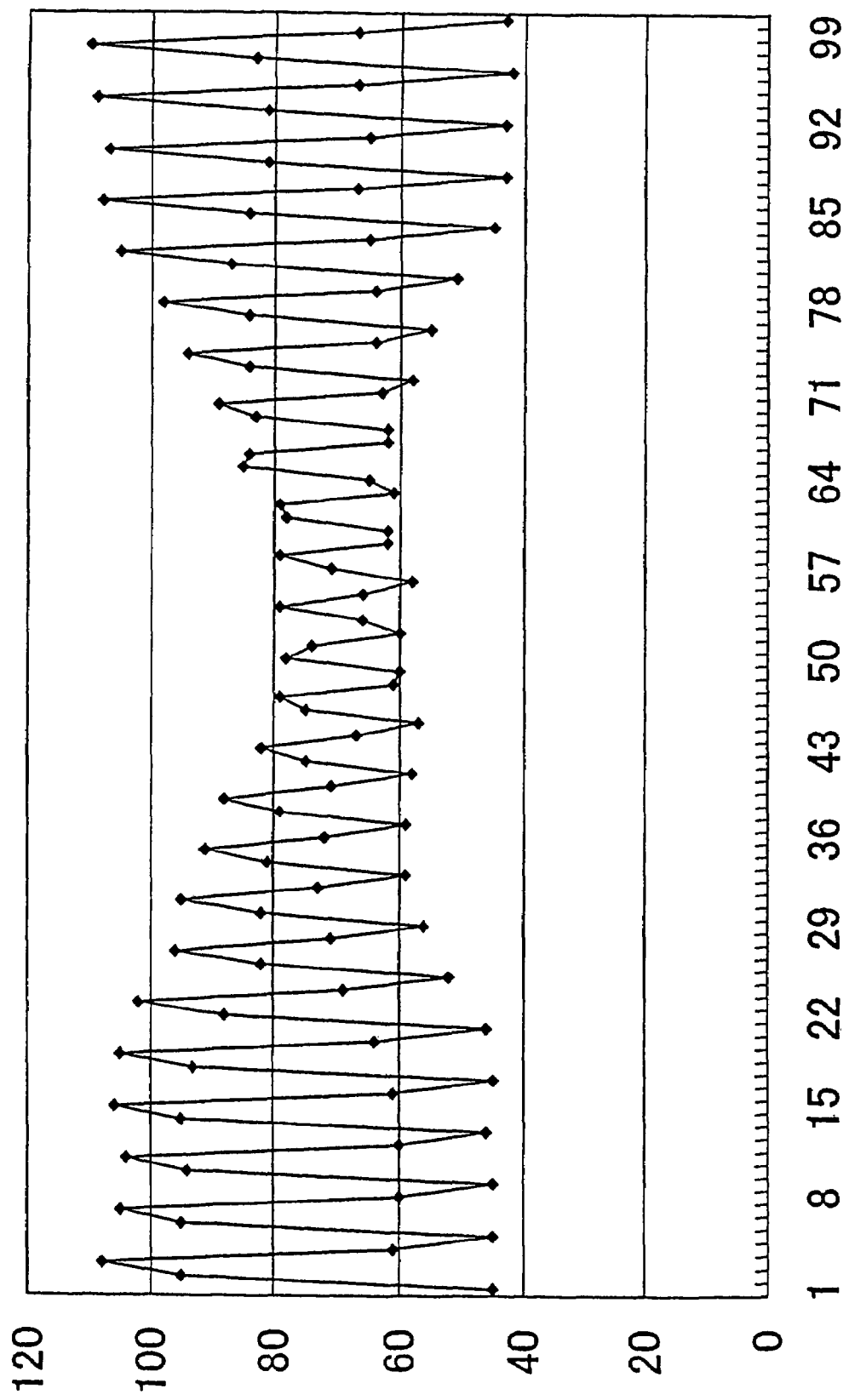
FIG. 16 is a partially enlarged view of the graph shown in FIG. 10.

Next, embodiments of the present invention will be described. According to the first embodiment, the gray data of the image picked-up by using the line sensor camera having 5000 pixels is inputted, as Z1 to Z5000, and a value of the inputted pixel output is expressed as Ci=Zi (i=1 to 5000). In the case of picking-up the image by four CCD pixels corresponding to one grid, FIG. 15 shows the portion of 1 to 1200 pixels of gray data, and FIG. 16 shows an enlarged view at an interval Q shown in FIG. 15.

The sequence for image processing will be described with reference to flowcharts shown in FIGS. 17 to 19. As shown in FIG. 17, the ± signs are generated in step 1. Reference symbol h denotes the number of pixels per grid (one pitch) and, then, the ± signs are generated based on a number h/2, Specifically, the number h/2 of the + signs and the number h/2 of the − signs are alternately generated. The generated signs are sequentially identified by fugo (k), and the generated signs are stored in a storage device, such as a register, a cache memory, or a main storage device. Sign generating means can perform the processing.

A flow shown in FIG. 17 shows an example of h=8, that is, the correspondence of 8 CCD pixels to each grid. However, in the flow, the number h, serving as an integral multiple of 4 can be applied to any number. For example, the number h may be 4 or 12. Specifically, in the example of h=8, four + signs and four − signs are alternately generated. In the case of h=4, two + signs and two − signs are alternately generated. In the case of h=12, six + signs and six − signs are alternately generated.

The number h increases, (as an integral multiple of 4) as described above, the number of CCD pixels per grid increases, and the precision for measurement is improved.

Figure 18:
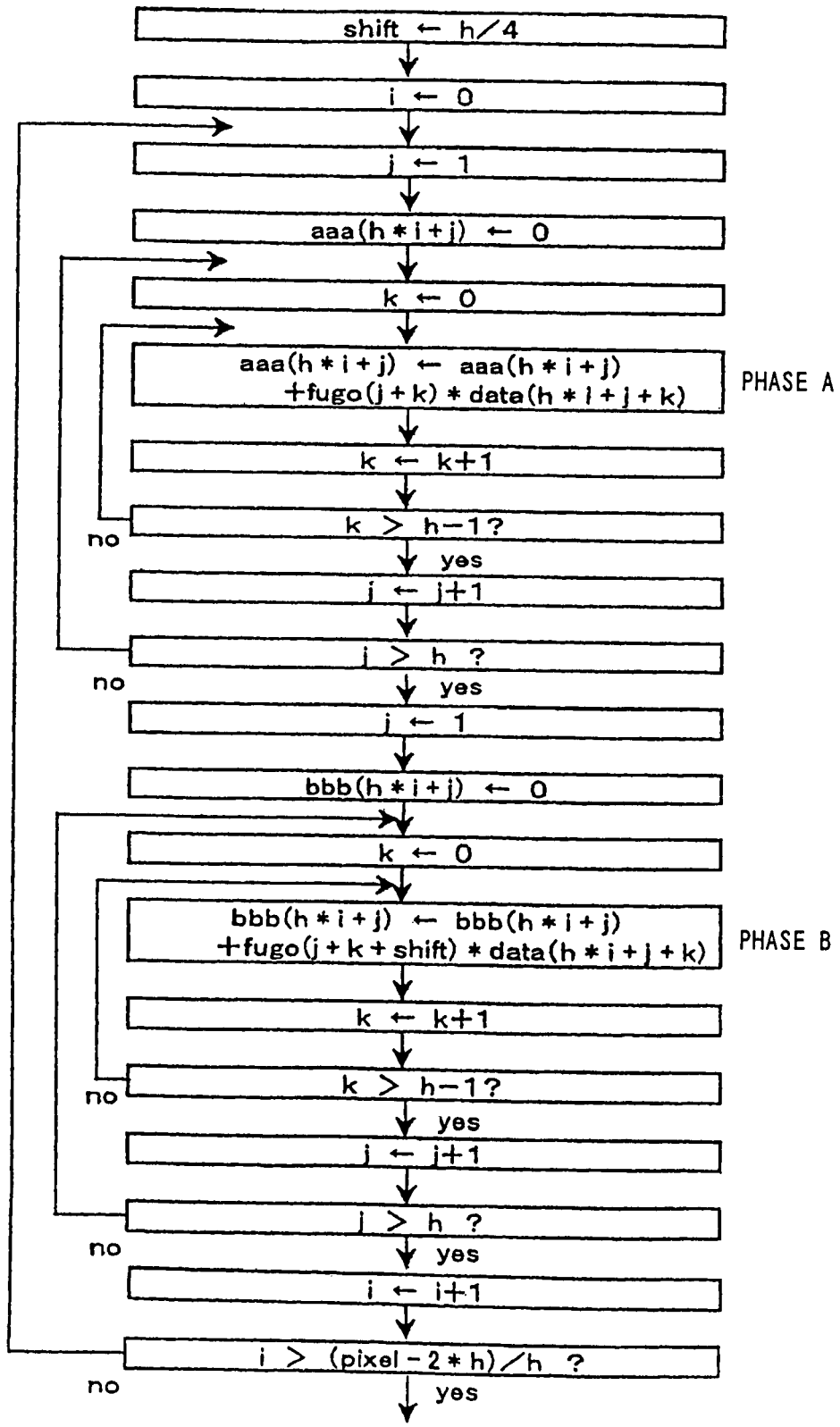
FIG. 18 is a flowchart showing another sequence of the image processing.

Next, as shown in FIG. 18, the sine waves with the phases A and B are generated in step 2. Specifically, the ± signs (fugo(k)) generated in step 1 are sequentially assigned to a value (data(i)) of the pixel output, and the value of the pixel output for phase A is calculated. A value Ai of the phase A to be obtained is calculated by the addition of values of pixel outputs with the signs for h pixels sequential to the value Ai.

Figure 20:
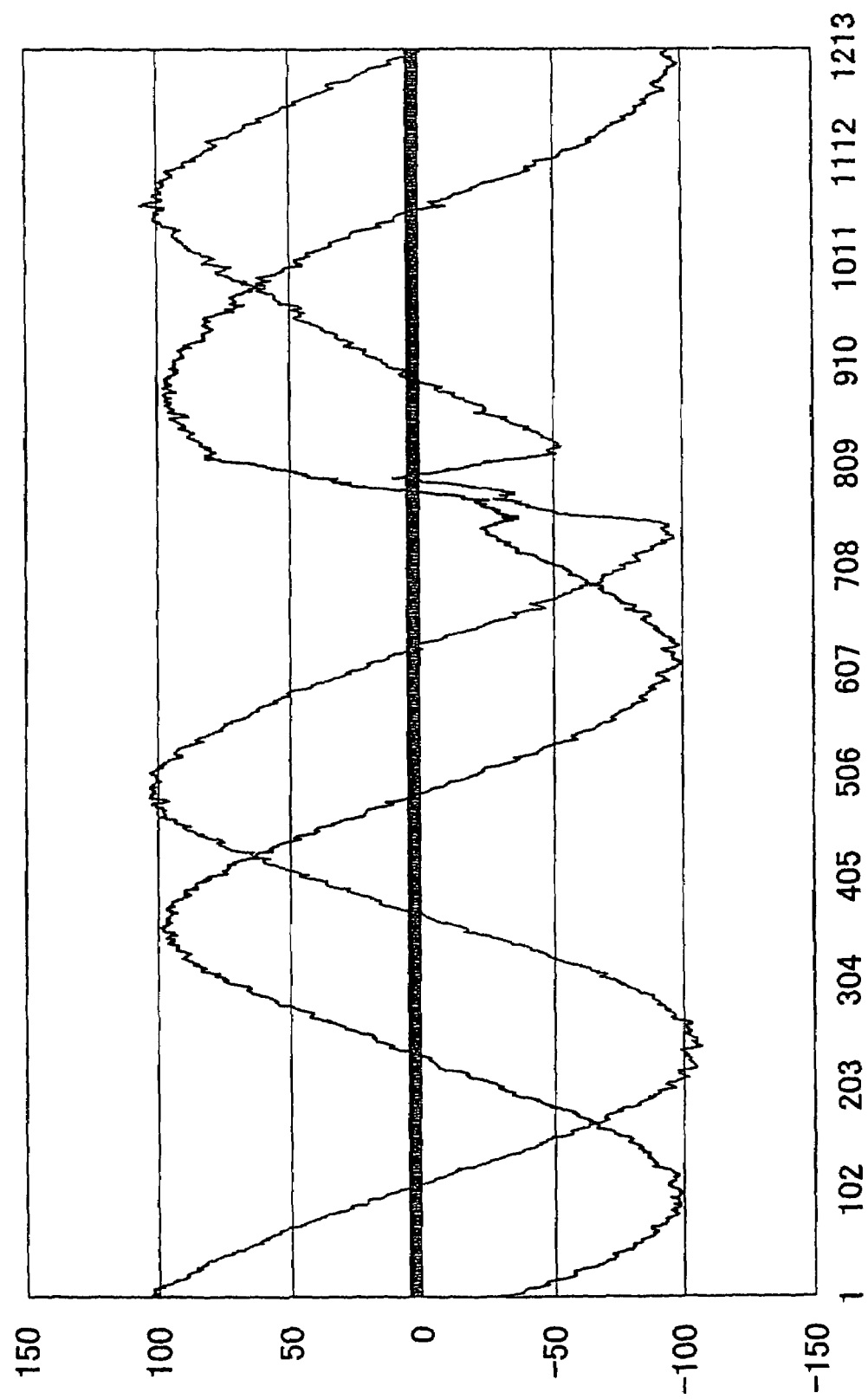
FIG. 20 is a diagram showing an example of a graph of sine waves with a phase A and a phase B.

Next, the phase B is calculated. the ± signs (fugo(k)) generated in step 1 are sequentially assigned to the values (data(i)) of the pixel outputs after the shift by h/4 pixels, and a value of the pixel output with the sign for phase B is calculated. A value Bi of the phase B to be obtained is calculated by the addition of the values of the pixel outputs with the signs for h pixels sequential to the value Bi. The calculated sine waves of the phases A and B are stored in the storage device. FIG. 20 shows a graph of the above-generated sine waves with the phases A and B. Sine-wave generating means can perform the processing. The generation of the signs and the generation of the sine waves with the phases A and B, on the other hand, can be processed by the following expression.

i=integer of 0 or more
k=0 to 5000/h
FOR i=0 To k $A8i+1=-C8i+1-C8i+2+C8i+3+C8i+4+C8i+5+C8i+6-C8i+7-C8i+8$ $A8i+2=-C8i+2+C8i+3+C8i+4+C8i+5+C8i+6-C8i+7-C8i+8-C8i+9$ $A8i+3=+C8i+3+C8i+4+C8i+5+C8i+6-C8i+7-C8i+8-C8i+9-C8i+10$ $A8i+4=+C8i+4+C8i+5+C8i+6-C8i+7-C8i+8-C8i+9-C8i+10+C8i+11$ $A8i+5=+C8i+5+C8i+6-C8i+7-C8i+8-C8i+9-C8i+10+C8i+11+C8i+12$ $A8i+6=+C8i+6-C8i+7-C8i+8-C8i+9-C8i+10+C8i+11+C8i+12+C8i+13$ $A8i+7=-C8i+7-C8i+8-C8i+9-C8i+10+C8i+11+C8i+12+C8i+13+C8i+14$ $A8i+8=-C8i+8-C8i+9-C8i+10+C8i+11+C8i+12+C8i+13+C8i+14-C8i+15$ $B8i+1=+C8i+1+C8i+2+C8i+3+C8i+4-C8i+5-C8i+6-C8i+7-C8i+8$ $B8i+2=+C8i+2+C8i+3+C8i+4-C8i+5-C8i+6-C8i+7-C8i+8+C8i+9$ $B8i+3=+C8i+3+C8i+4-C8i+5-C8i+6-C8i+7-C8i+8+C8i+8+C8i+9+C8i+10$ $B8i+4=+C8i+4-C8i+5-C8i+6-C8i+7-C8i+8+C8i+9+C8i+10+C8i+11$ $B8i+5=-C8i+5-C8i+6-C8i+7-C8i+8+C8i+9+C8i+10+C8i+11+C8i+12$ $B8i+6=-C8i+6-C8i+7-C8i+8+C8i+9+C8i+10+C8i+11+C8i+12-C8i+13$ $B8i+7=-C8i+7-C8i+8+C8i+9+C8i+10+C8i+11+C8i+12-C8i+13-C8i+14$ $B8i+8=-C8i+8+C8i+9+C8i+10+C8i+11+C8i+12-C8i+13-C8i+14-C8i+15$  (Expression 4)

Figure 19:
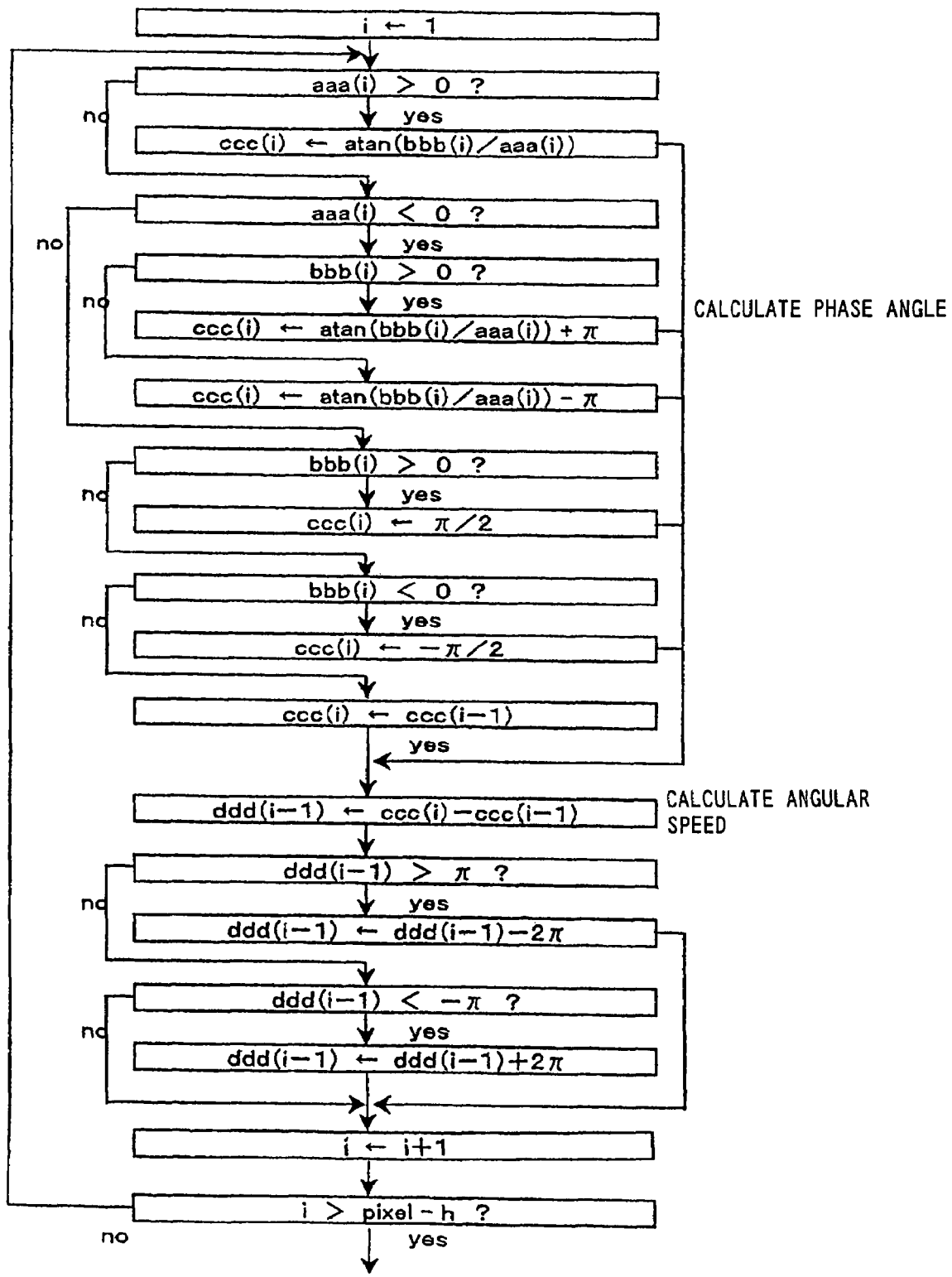
FIG. 19 is a flowchart showing another sequence of the image processing.
Figure 21:
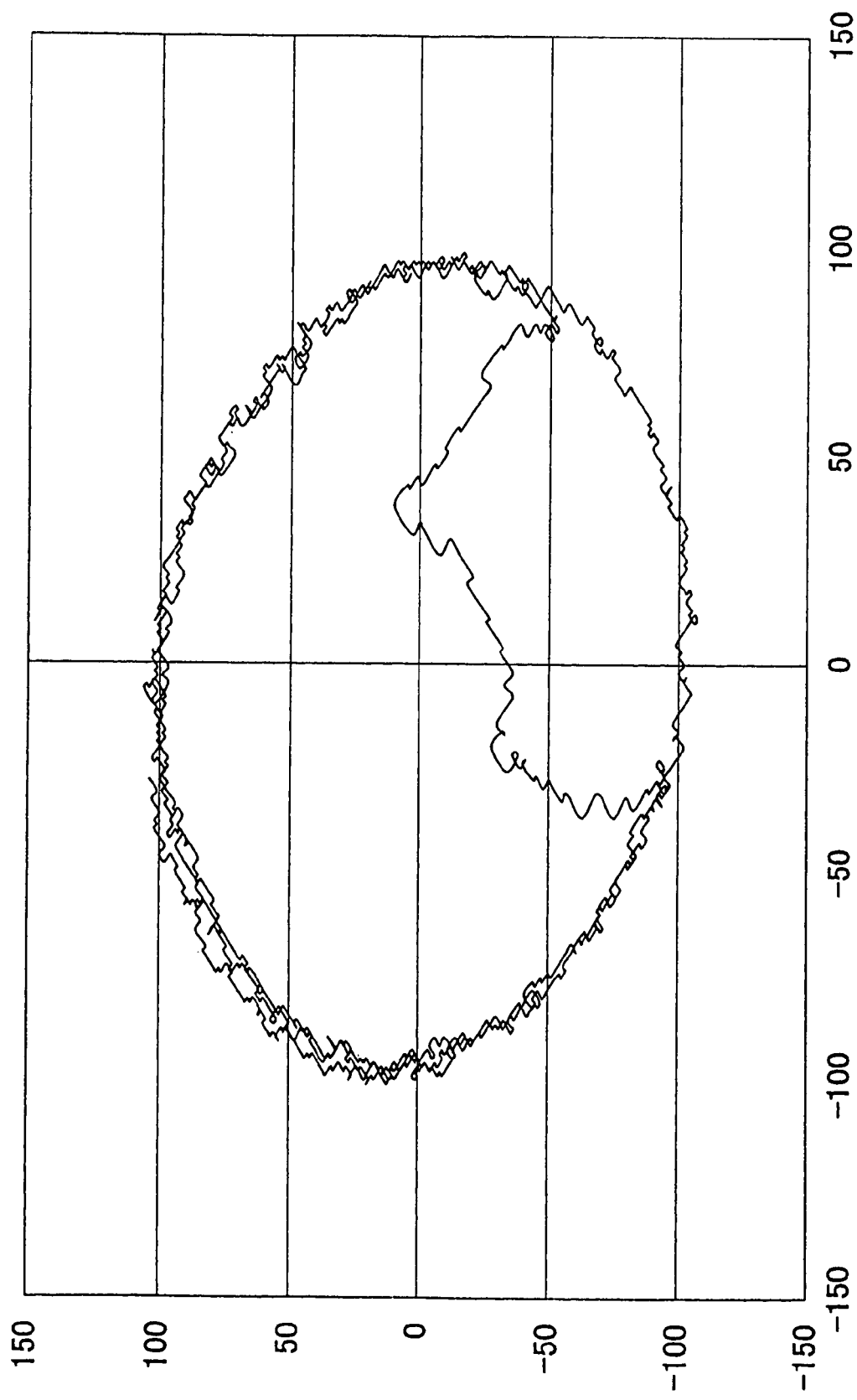
FIG. 21 is a diagram showing an example of the Lissajous figure obtained by the sine waves with the phase A and the phase B.
Figure 22:
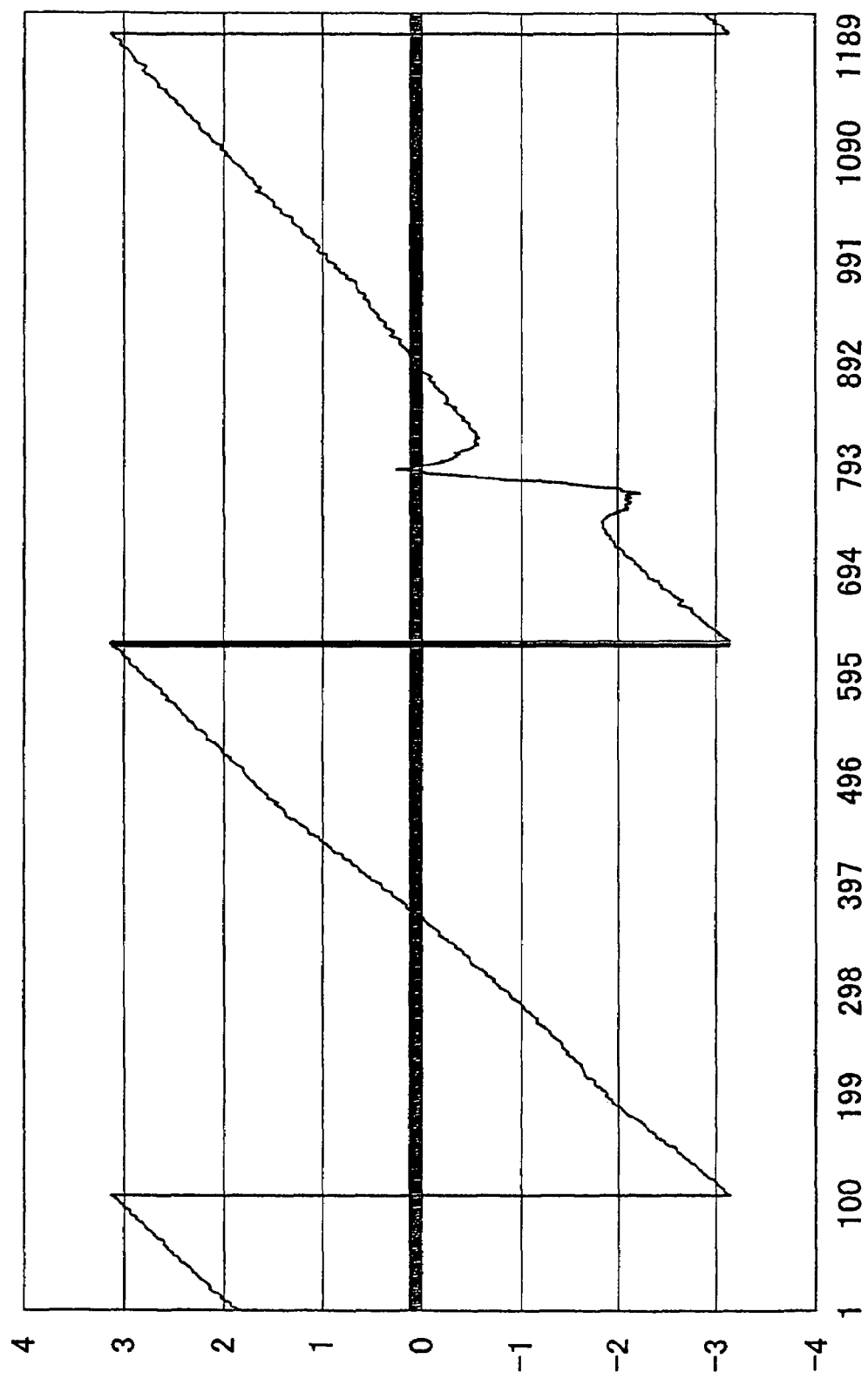
FIG. 22 is a diagram showing an example of a graph of a phase angle on the Lissajous figure.

Next, referring to FIG. 19, in step 3, the phase angle is calculated and the angular speed is calculated. First, FIG. 21 shows the Lissajous figure obtained by the sine waves with the phases A and B as generated above. Incidentally, the Lissajous figure is used for convenience's sake of a description, and the phase angle on the Lissajous figure is calculated to be obtained. Therefore, the processing for drawing the above-mentioned Lissajous figure is not necessarily required. Next, the following expression enables the calculation of the phase angle on the Lissajous figure of the pixels obtained from the sine waves with the phases A and B. The calculating result is stored in the storage device. Phase angle calculating means can perform the processing. FIG. 22 shows the phase angle on the Lissajous figure.

(Expression 5)

Calculation of the phase angle on the Lissajous figure obtained from the sine curves of the phases A and B

| | |
|---|---|
| IF (A1>0) THEN C1=ATAN(B1/A1) | 1ST QUADRANT, 4TH QUADRANT |
| ELSE IF (A1<0) THEN | |
| IF (B1>0) THEN C1=ATAN(B1/A1)+π | 2ND QUADRANT |
| ELSE C1=ATAN(B1/A1)−π | 3RD QUADRANT |
| ELSE IF (B1>0) THEN C1=π/2 | 2ND QUADRANT (except-processing of A1=0) |
| ELSE IF (B1<0) THEN C1=−π/2 | 4TH QUADRANT (except-processing of A1=0) |
| ELSE C1=0 | (except-processing of A1=0 and B1=0) |
| i=2 TO 4996 | |
| IF (Ai>0) THEN Ci=ATAN(Bi/Ai) | 1ST QUADRANT, 4TH QUADRANT |
| ELSE IF (Ai<0) THEN | |
| IF (Bi>0) THEN Ci=ATAN(Bi/Ai)+π | 2ND QUADRANT |
| ELSE Ci=ATAN(Bi/Ai)−π | 3RD QUADRANT |
| ELSE IF (Bi>0) THEN Ci=π/2 | 2ND QUADRANT (except-processing of Ai=0) |
| ELSE IF (Bi<0) THEN Ci=−π/2 | 4TH QUADRANT (except-processing of Ai=0) |
| ELSE Ci=Ci−1 | (except-processing of Ai=0 and Bi=0) |

Figure 23:
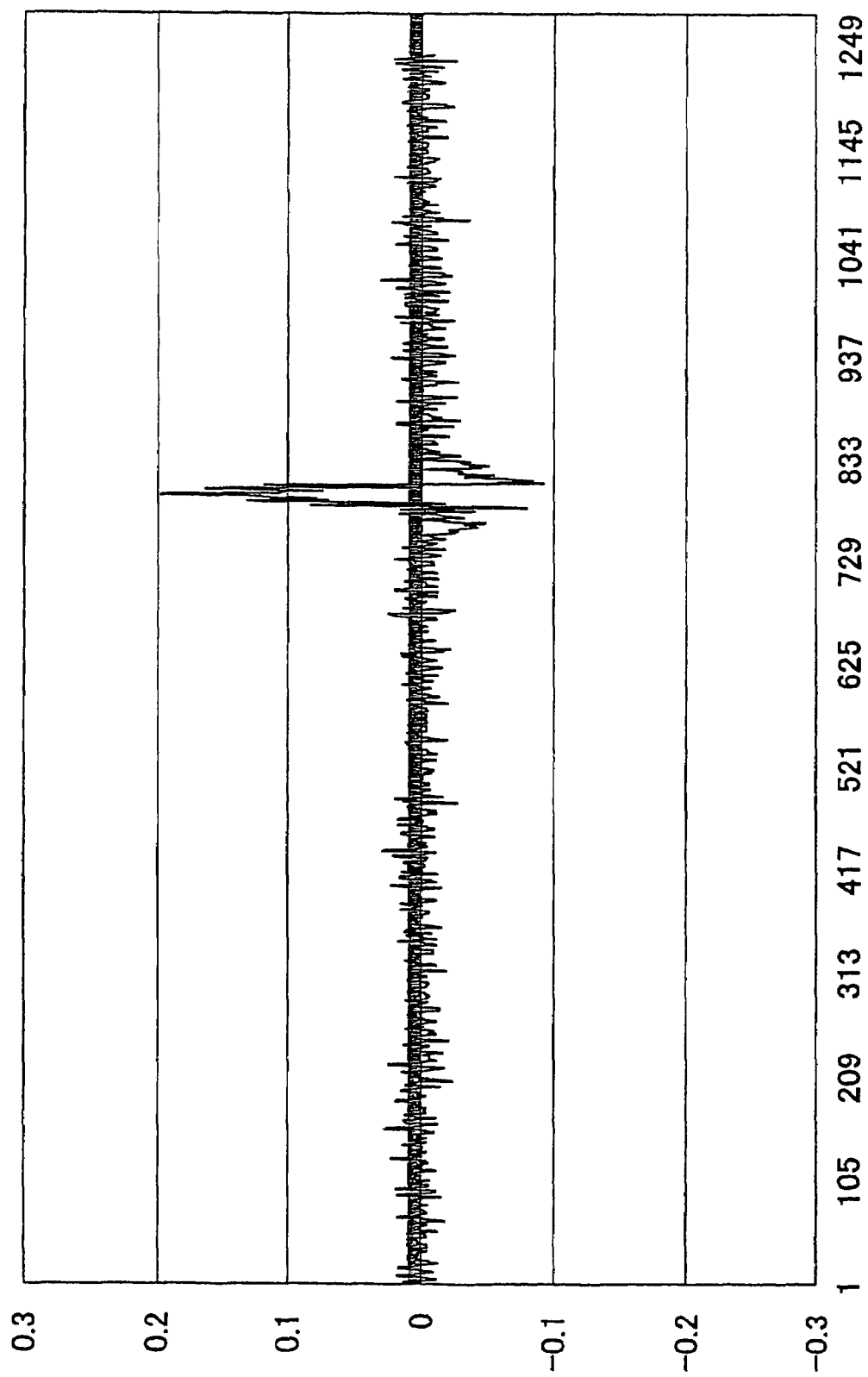
FIG. 23 is a diagram showing an example of a graph of a phase angular speed.
Figure 25:
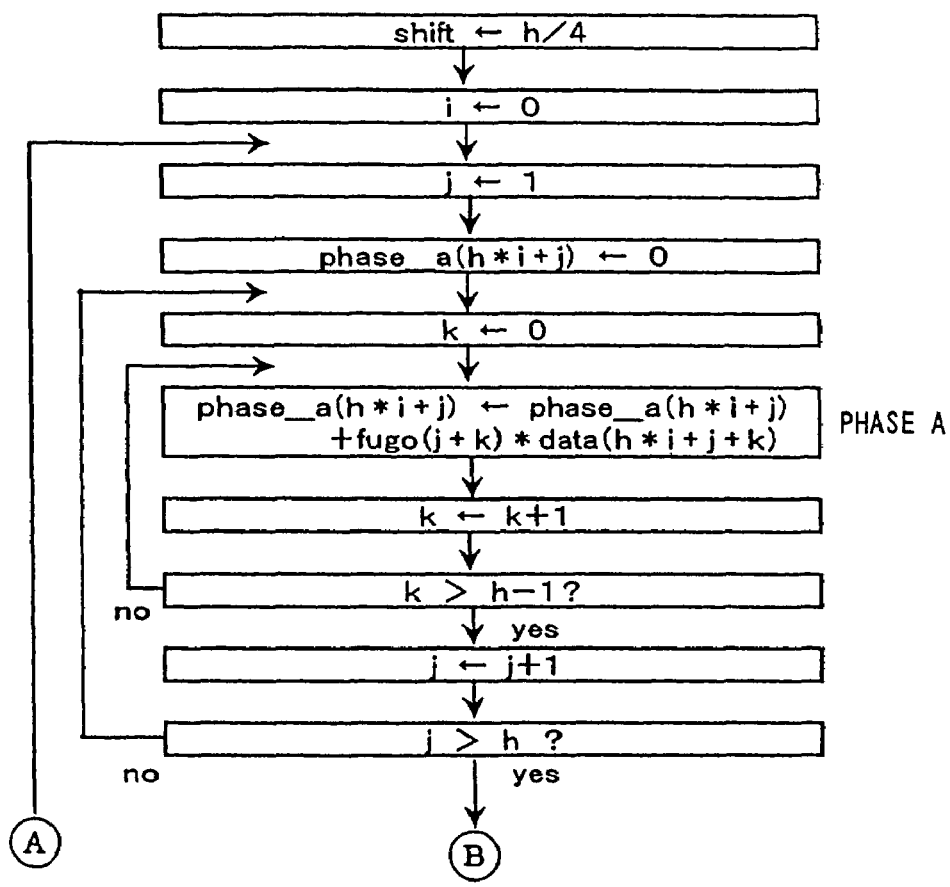
FIG. 25 is a flowchart showing another sequence of the image processing.
Figure 26:
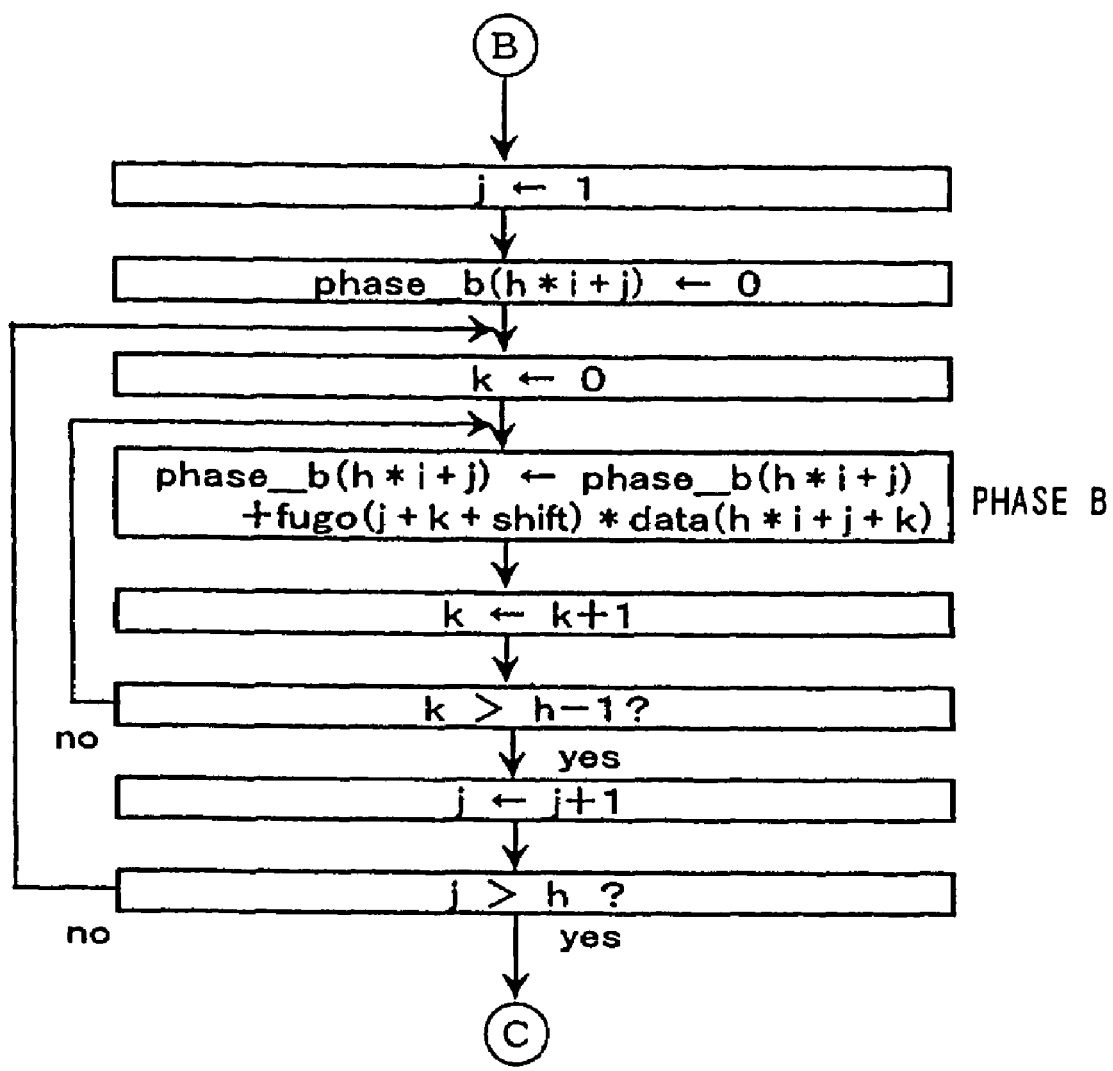
FIG. 26 is a flowchart showing another sequence of the image processing.
Figure 27:
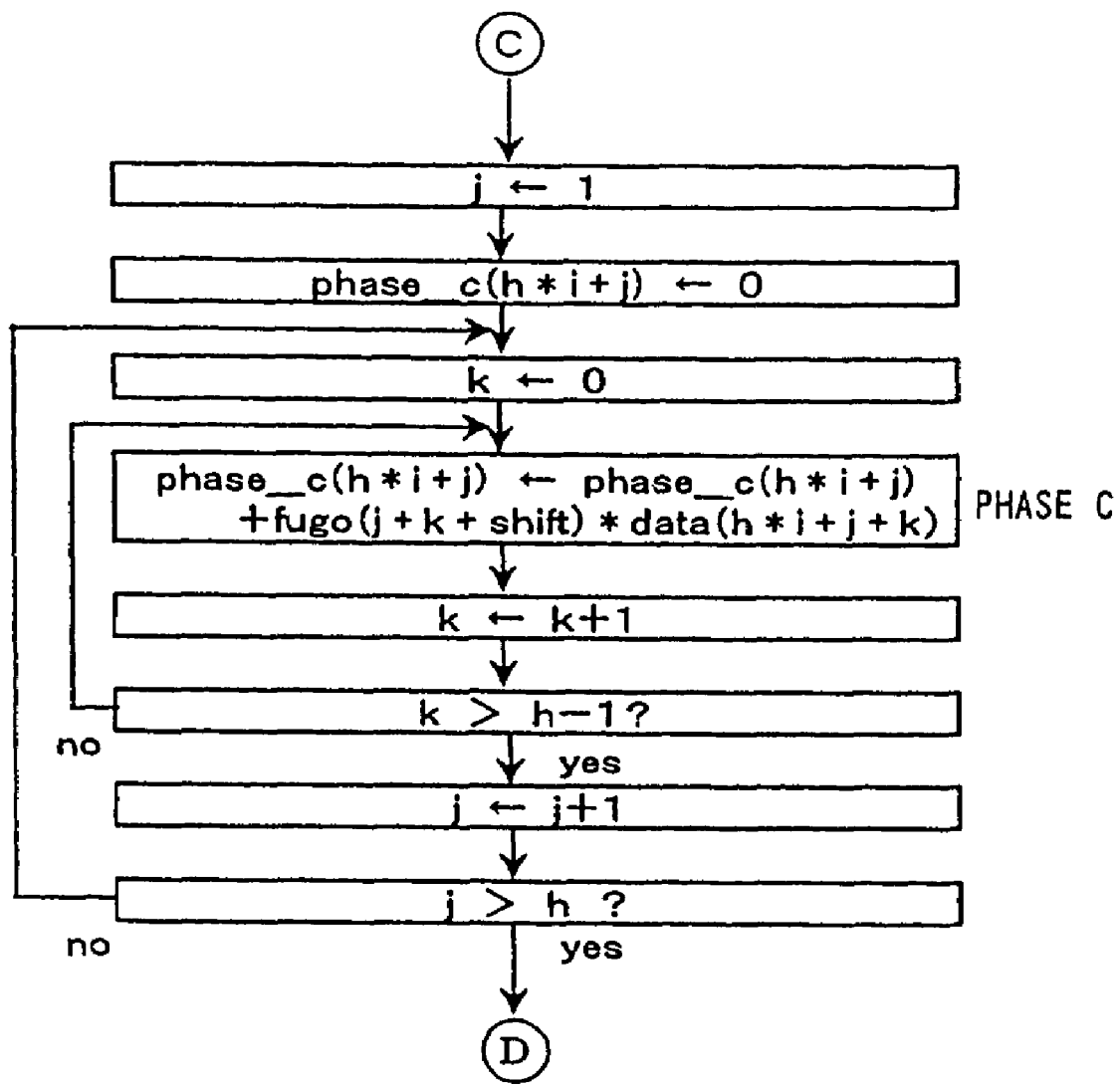
FIG. 27 is a flowchart showing another sequence of the image processing.
Figure 28:
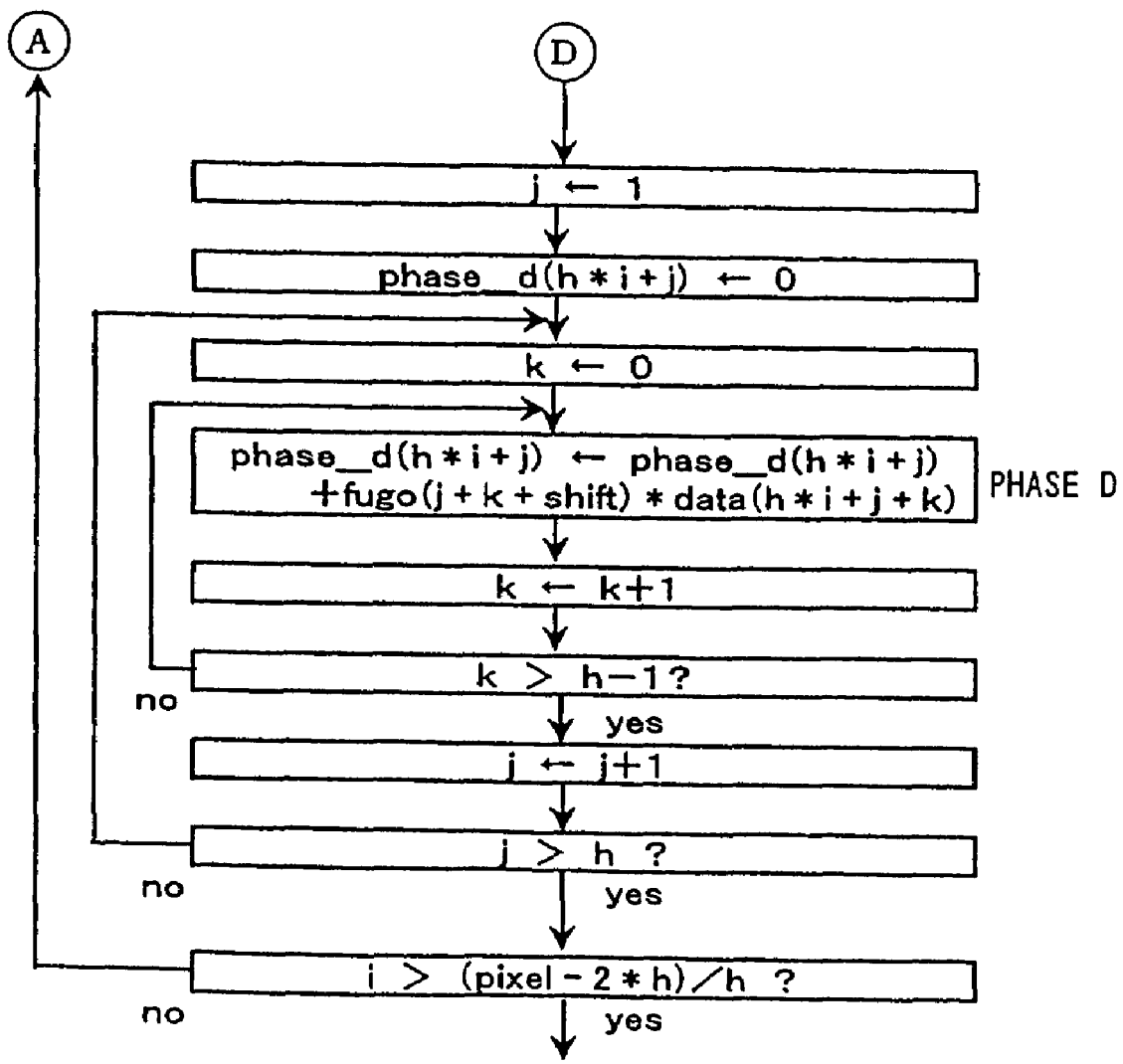
FIG. 28 is a flowchart showing another sequence of the image processing.

Next, the rate of change of the phase angle per pixel, that is, the phase angular speed is calculated by using the phase angle on the Lissajous figure of the obtained pixels based on the following expression. Then, the calculating result is stored in the storage device. Angular speed calculating means can perform the processing. FIG. 23 shows the obtained phase angular speed.

(Expression 6)

Calculation of the rate of change of phase angle per pixel, that is, phase angular speed

| | |
|---|---|
| Di−1=Ci−Ci−1 | Rate of phase change per pixel |
| IF (Di−1>π THEN Di−1=Di−1−2π | Correct in (−) direction at 1 period. |
| IF (Di−1<−π) then Di−1=Di−1+2π | Correct in (+) direction at 1 period |

Next, the obtained phase angular speed per pixel is averaged and is zero-corrected. Then, the calculating result is stored in the storage device. Correcting means can perform the processing.

(Expression 7)

Averaging and Zero-correction

The moire fringes are generated from the deviation in pitches between the grid and the CCD pixel and Di is shifted from zero at the angular speed of the phase angle corresponding to the amount of deviation. Therefore, all the phase angular speeds need to be averaged and the deviation needs to be corrected to set the deviation to be at the zero level.

$AVE = \Sigma Di/4995$ i=1 to 4995

Ei=Di−AVE Rate of phase change per pixel after correction

Next, the refractive power at the pixel is calculated by using the corrected phase angular speed based on the following expression. Then, the calculated result is stored in the storage device. Refractive-power calculating means can perform the processing.

(Expression 8)

Calculation of lens power

LP: Lens power (unit: dpt (diopter))

f: Focusing distance

P: Pitch of grid

L: Length between glass and grid

θ: Refractive angle due to glass, then,

Amount of deviation by one pixel at an i-th pixel=$(Ei/2\pi) \cdot P$

Angle of deviation by one pixel at the i-th pixel:

$\theta i = \tan \theta i = (Ei/2\pi) \times P \times (1/L)$ (Because θi is small), A relation between Pitch of one pixel: G=P/4, and focusing distance fi of lens operation at the portion is $\tan \theta i = G/fi$, therefore, $LPi = 1/fi = \tan \theta i/G = (Ei/2\pi) \times P \times (1/L) \times (4/P) = 2 \times Ei/(\pi \times L)$ The refractive power LPi is multiplied by 1000, thereby obtaining a unit of mdpt.

Next, an integrated value of the amount of deviation at the pixel is calculated by using the corrected phase angular speed by the following expression. Then, the calculated result is stored in the storage device. Deviation integrating means can perform the processing.

(Expression 9)

Calculation of the Integrated Value of the Amount of Deviation (Angle at the Phase) at the Pixel The values Ei are integrated to obtain the integrated amount of deviations of the phase angle on the Lissajous figure at the pixels.

A bending angle of light at the pixel can be obtained from Fi.

$F1=0$ i=2 to 4992

$Fi+1=Fi+Ei$

In the example as shown in the flowchart shown in FIG. 17, the number h/2 of the + signs and a number h/2 of the − signs are alternately generated. The generated ± signs are shifted by 4/h signs, then, are sequentially assigned to the values of the pixel outputs, and the value of the pixel output with the signs for phase B is obtained. Even in the case of increasing the number of CCD pixels corresponding to one grid, as long as the number of CCD pixels is an integral multiple of 4, the above-mentioned sign assigning processing is performed, thereby obtaining the two sine waves with the phases A and B, detecting the defect, and the calculating the refractive power, or the like. Therefore, the number of pixels corresponding to one grid increases and the precision for measurement rises.

Further, when the number X of pixels corresponding to one grid is equal to 4p (where reference symbol p is an integer of 1 or more), the expression for obtaining the phase A (An) from a value ACk of the pixel output with the sign for sine wave A is generalized as follows.

$$An = \sum_{k=n}^{n+(X-1)} ACk \qquad \text{(Expression 10)}$$

Similarly, when X=4p, the expression for obtaining the phase B (Bn) from a value BCk of the pixel output with the sign for sine waves B is generalized as follows.

$$Bn = \sum_{k=n}^{n+(X-1)} BCk \quad \text{(Expression 11)}$$

Second Embodiment

A description is given of another method for obtaining the phase angle at the pixel by the CCD output with the corresponding state of $4n\pm\alpha$ CCD pixels to n grids according to the second embodiment of the present invention.

According to the second embodiment, four types of sine waves comprising phases A to D are obtained based on the output of the CCD pixel having the moire fringes. The phase angles are obtained by using the four types of sine waves. The four types of sine waves are sequentially obtained by deviating the phases at an angle of 90° in the order of the phase A, phase B, phase C, and phase D. That is, the phase B is obtained by deviating the phase at an angle of 90° from the phase A, the phase C is obtained by deviating the phase at an angle of 90° from the phase B, and the phase D is obtained by deviating the phase at an angle of 90° from the phase C.

Next, a description is given of a method for obtaining the four types of sine waves deviated in phase from each other at an angle of 90° based on the output of the CCD pixel.

(Step 1)

First, the positive or negative sign is assigned to an output (Vn) of the CCD pixel under a predetermined rule. Specifically, similarly to the first embodiment, all pixels are divided into continuous groups having four continuous pixels. Then, the pixels in the group are designated by $V4i+1$, $V4i+2$, $V4i+3$, and $V4i+4$ ($0 \leq i$).

Next, the signs in the row included in the following Table 2 are multiplied for four pixels included in the group by the sequential pattern. Specifically, a row 1 is used for the phase A, and the signs in I to IV in the row 1 correspond to the four pixels in the group and are multiplied. For the phase B, the signs in a row 2 correspond to the four pixels in the group and are multiplied. For the phase C, the signs in a row 3 are similarly multiplied. Finally, for the phase D, the signs in a row 4 are similarly multiplied.

TABLE 2

|   | I | II | III | IV |
|---|---|----|-----|----|
| 1 | + | +  | −   | −  |
| 2 | + | −  | −   | +  |
| 3 | − | −  | +   | +  |
| 4 | − | +  | +   | −  |

In Table 2, the sign patterns included in the rows are varied depending on the rows, and the sign arrangements in the sign pattern are shifted by one sign in the rows 1 to 4. Therefore, the rows 1 to 4 are sequentially assigned to the phases A to D, thereby shifting the sign pattern for multiplication by one sign. Importantly, the signs are shifted by one sign in the phases A to D but the row 1 is not necessarily assigned to the phase A. Therefore, any of the rows 1 to 4 may be assigned to the phase A. Table 3 shows an example of sign pattern assignment to the phases A to D.

TABLE 3

| 1 | A | D | C | B |
| 2 | B | A | D | C |
| 3 | C | B | A | D |
| 4 | D | C | B | A |

As described above, the + or − sign is multiplied, for sign operation, to all the values of pixel outputs under the rule, and four values (AVk, BVk, CVk, and DVk) of the pixel outputs with the signs for phase A, phase B, phase C, phase D are obtained. Sign assigning means of the image processing means 5 can perform the processing for calculating the values of the four types of the pixel output with the signs for phases A to D.

(Step 2)

Next, the four types of sine waves with the phase A, phase B, phase C, phase D are calculated. The sine waves to the values of four types of pixel outputs with the signs for the phases A to D are obtained by the following expression. Sine-wave generating means of the image processing means 5 can perform the processing for calculating the four types of sine waves with the phase A, phase B, phase C, phase D.

The sine wave with the phase A is obtained, with the value of the pixel output with the sign for the phase A, by the following expression.

$$An = \sum_{k=n}^{n+3} AVk \quad \text{(Expression 12)}$$

(where reference symbol An denotes the phase A and reference symbol AVk denotes the value of the pixel output with symbol for a k-th pixel).

Subsequently, the sine wave with the phase B is obtained, with the value of the pixel output with the sign for the phase B, by the following expression.

$$Bn = \sum_{k=n}^{n+3} BVk \quad \text{(Expression 13)}$$

(where reference symbol Bn denotes the phase B and reference symbol BVk denotes the value of the pixel output with symbol for the k-th pixel).

Subsequently, the sine wave with the phase C is obtained, with to the value of the pixel output with the sign for the phase C, by the following expression.

$$Cn = \sum_{k=n}^{n+3} CVk \quad \text{(Expression 14)}$$

(where reference symbol Cn denotes the phase C and reference symbol CVk denotes the value of the pixel output with symbol for the k-th pixel).

Subsequently, the sine wave with the phase D is obtained, with the value of the pixel output with the sign for the phase D, by the following expression.

$$Dn = \sum_{k=n}^{n+3} DVk \quad \text{(Expression 15)}$$

(where reference symbol Dn denotes the phase D and reference symbol DVk denotes the value of the pixel output with symbol for the k-th pixel).

Further, in the case of X=4, the above-mentioned processing for assigning the signs by grouping and obtaining the phases A to D is expressed by the following expression.

i=integer of 0 or more.

$A4i+1=-V4i+1+V4i+2+V4i+3-V4i+4$ $A4i+2=+V4i+2+V4i+3-V4i+4-V4i+5$ $A4i+3=+V4i+3-V4i+4-V4i+5+V4i+6$ $A4i+4=-V4i+4-V4i+5+V4i+6+V4i+7$ $B4i+1=+V4i+1+V4i+2-V4i+3-V4i+4$ $B4i+2=+V4i+2-V4i+3-V4i+4+V4i+5$ $B4i+3=-V4i+3-V4i+4+V4i+5+V4i+6$ $B4i+4=-V4i+4+V4i+5+V4i+6-V4i+7$ $C4i+1=+V4i+1-V4i+2-V4i+3+V4i+4$ $C4i+2=-V4i+2-V4i+3+V4i+4+V4i+5$ $C4i+3=-V4i+3+V4i+4+V4i+5-V4i+6$ $C4i+4=+V4i+4+V4i+5-V4i+6-V4i+7$ $D4i+1=-V4i+1-V4i+2+V4i+3+V4i+4$ $D4i+2=-V4i+2+V4i+3+V4i+4-V4i+5$ $D4i+3=+V4i+3+V4i+4-V4i+5-V4i+6$ $D4i+4=+V4i+4-V4i+5-V4i+6+V4i+7$ \quad (Expression 16)

Next, the phase angles of the pixels are obtained based on the above-obtained sine waves with the phases A to D. When reference symbol Hi denotes the phase angle at the pixel, the phase angle is obtained by an equation of Hi=ATAN((Bi−Di)/(Ai−Ci)). Phase angle calculating means of the image processing means 5 can perform the above-mentioned processing for calculating the phase angle.

Second Embodiment

Next, a description is given of the second embodiment of the present invention using the four types of sine waves with the phases A to D. According to the second embodiment, a description is given of an example of processing the gray data of the image picked-up by using a line sensor camera having 5000 pixels.

The sequence for imaging processing will be described with reference to flowcharts shown in FIGS. 24 to 29. FIGS. 24 to 29 are flowcharts showing the sequence for imagining processing. Referring to FIG. 24, the ± signs are generated in step 1. Reference symbol h denotes the number of pixels per grid (one pitch) and, then, the ± signs are generated based on the number h/2. Specifically, the number h/2 of + signs and the number h/2 of − signs are alternately generated. The generated signs are sequentially identified by fugo (k), and the generated signs are stored in a storage device, such as a register, a cache memory, or a main storage device. Sign generating means can perform the processing.

A flow shown in FIG. 24 shows an example of h=4, that is, the correspondence of 4 CCD pixels to each one grid. However, in the flow, the number h which is an integral multiple of 4 can be applied to any number. For example, the number h may be 8 or 12. Specifically, in the example of h=4, two + signs and two − signs are alternately generated. In the case of h=8, four + signs and four − signs are alternately generated. In the case of h=12, six + signs and six − signs are alternately generated.

The number h increases, (as an integral multiple of 4), as mentioned above, the number of CCD pixels per one grid increases, and the precision for measurement rises.

Next, referring to FIGS. 25 to 28, sine waves with the phases A to D are generated in step 2. Specifically, the ± signs (fugo(k)) generated in step 1 are sequentially assigned to a value (data(i)) of the pixel output, and the value of the pixel output for phase A is calculated. A value of the phase A (phase_a(i)) to be obtained is calculated by the addition of values of pixel outputs with the signs for h pixels after the i-th pixel.

Figure 30:
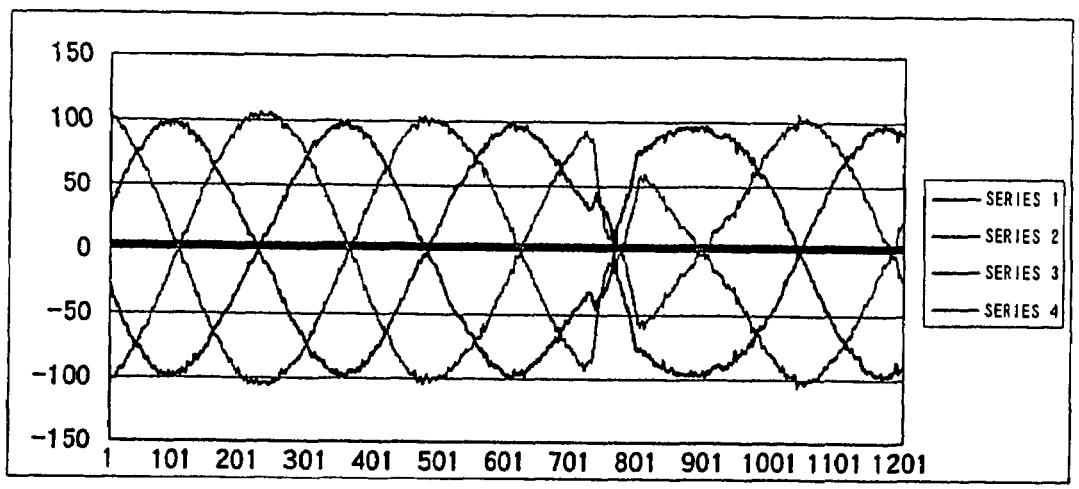
FIG. 30 is a diagram showing an example of a graph of sine waves with phases A to D.

Next, the phase B is calculated. the ± signs (fugo(k)) generated in step 1 are sequentially assigned to the values (data(i)) of the pixel outputs after the shift operation by h/4 pixels, and a value of the pixel output with the sign for phase B is calculated. A value of the phase B ((phase_b(i)) to be obtained is calculated by the addition of the values of the pixel outputs with the signs for h pixels after the i-th pixel. Similarly, a value of the phase C ((phase_c(i)) is calculated and a value of the phase D ((phase_d(i)) is then calculated. The calculated sine waves with the phases A to D are stored in the storage device. FIG. 30 shows a graph of the above-generated sine waves with the phases A to D. Sine-wave generating means can perform the processing.

Figure 29:
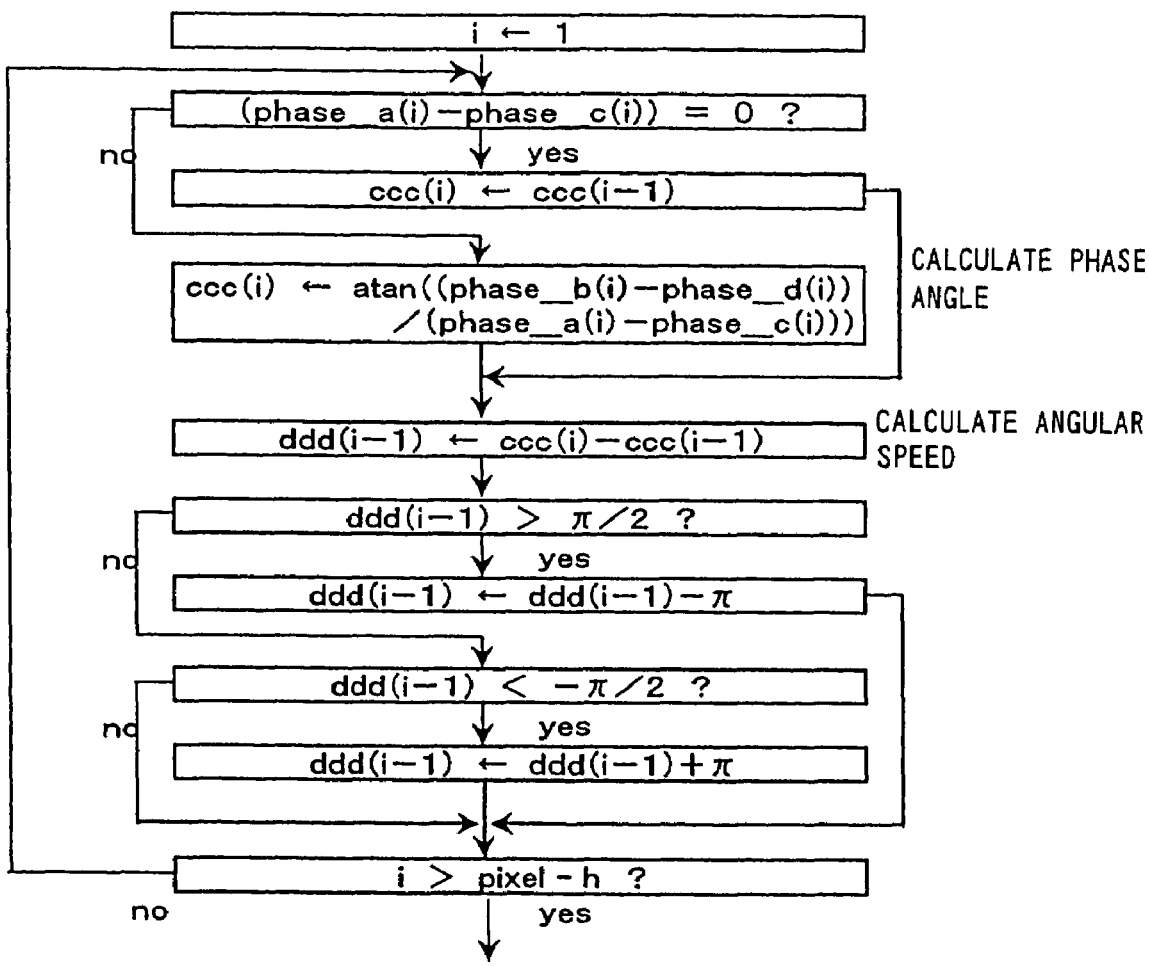
FIG. 29 is a flowchart showing another sequence of the image processing.
Figure 31:
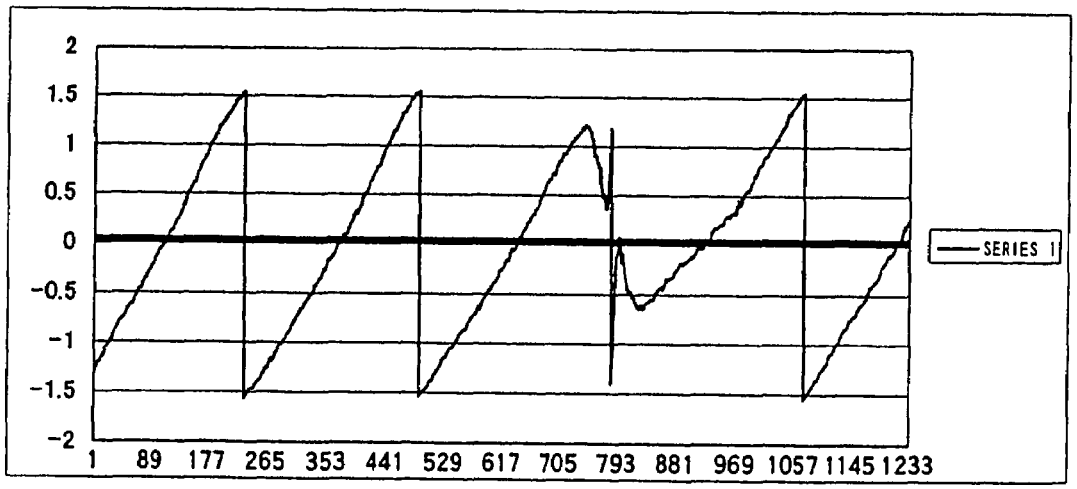
FIG. 31 is a diagram showing an example of a graph of a phase angle.

Referring to FIG. 29, the phase angle is calculated in step 3, and the angular speed is calculated. The phase angle is calculated based on the above-mentioned four types of sine waves with the phases A to D by the following expression. FIG. 31 shows a graph of the calculated phase angle.

Calculation of phase angle $Ci=\text{ATAN}((PBi-PDi)/(PAi-PCi))$, $Ci=Ci-1$ if $(PAi-PCi)$ is equal to 0. \quad (Expression 17)

In the calculation, Ci is distributed from $-\pi/2$ to $\pi/2$.

In the calculating method of the phase angle according to the second embodiment, the number of IF sentences is reduced to increase the calculating processing in speed, as compared with that according to the first embodiment.

Figure 32:
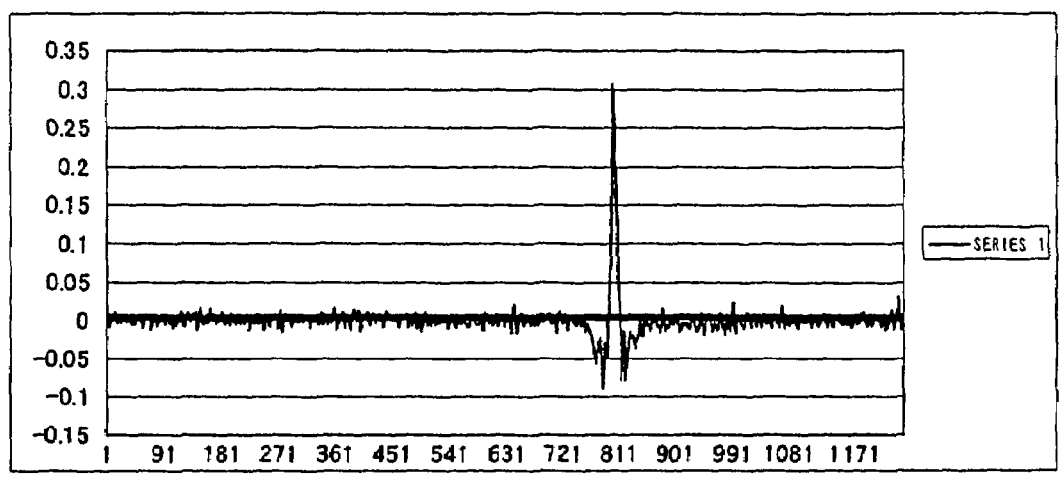
FIG. 32 is a diagram showing an example of a graph of a phase angular speed.

Next, the rate of change of the phase angle per pixel, that is, the phase angular speed is calculated by using the obtained phase angle based on the following expression. Then, the calculating result is stored in the storage device. Angular speed calculating means can perform the processing. FIG. 32 shows the obtained phase angular speed.

(Expression 18)

| | |
|---|---|
| Di−1=Ci−Ci−1 | Rate of phase change per pixel |
| IF (Di−1>π/2) THEN Di−1=Di−1−π | Correct in (−) direction at half period. |
| IF (Di−1<−π/2) then Di−1=Di−1+π | Correct in (+) direction at half period. |

Next, the obtained phase angular speed per pixel is averaged and is zero-corrected. Then, the calculating result is stored in the storage device. Correcting means can perform the processing.

(Expression 19)

Average and Zero-correction

The moire fringes are generated from the deviation in pitches between the grid and the CCD pixel in the case of non-matching and deviating the pitch between the grid and the CCD element, and D is shifted from zero, depending on the angular speed of the angle of the difference between the phases corresponding to the deviation. Therefore, all the phase angular speeds need to be averaged and the deviation needs to be corrected to set the deviation to be at the zero level.

$$AVE=\Sigma Di/4995$$

i=1 to 4995

Ei=Di−AVE Rate of Phase Change per Pixel

Next, the refractive power at the pixel is calculated by using the corrected phase angular speed. The specific calculating processing is the same as that according to the first embodiment and a detailed description is therefore omitted.

Figure 33:
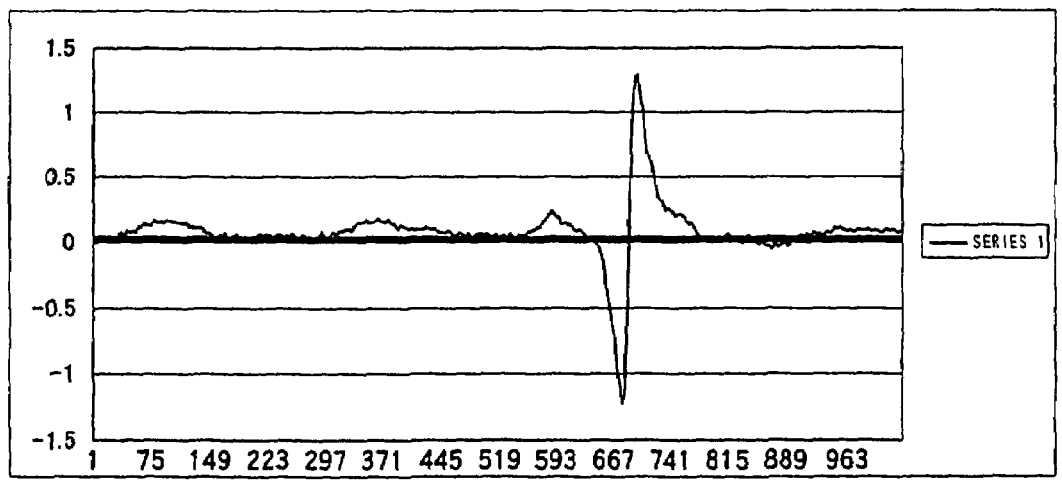
FIG. 33 is a diagram showing an example of a graph for integrating an angular speed (lens power), indicating a refractive angle of light by lens operation.

Next, an integrated value of the amount of deviation at the pixel is calculated by using the corrected phase angular speed by the following expression. Then, the calculating result is stored in the storage device. Deviation integrating means can perform the processing. FIG. 33 shows a graph of a value Fi obtained based on the following expression. The graph of the value Fi is a graph for integrating the angular speed (lens power), and the value Fi becomes the refractive angle of light as a result of lens operation.

Average of Four Pixels i=1 to 4992

$$Fi=(Ei+Ei+1+Ei+2+Ei+3)/4 \quad \text{(Expression 20)}$$

(The subsequent calculation may be performed, not by the division by 4, but only by the addition).

Third Embodiment

As described above according to the first and second embodiments, the detecting method of the optical distortion of the defect using the moire fringes uses the grid pattern to generate the moire fringes. Further, the optical distortion of the defect in the array direction of girds is detected. Thus, the size of detectable defect is determined depending on the interval between the grid patterns and the camera for image pickup operation.

In order to detect the defect with minute size, the interval between the grid patterns is narrowed, and the resolution of camera is increased, thereby realizing the detection. However, since the field of view of each camera is narrow, the number of cameras increases, the detector is large, and the costs increase.

Therefore, in the detecting method of a minute chipped-portion existing on the plate member, it is preferable to provide a detector that obtains the detecting sensitivity higher than those in the methods according to the first and second embodiment under the same conditions (interval between the grid patterns and the resolution of camera) as those according to the first and second embodiments.

According to the third embodiment, it is pointed that the chipped portion existing on the plate member is detected by using the grid pattern and a slit, in addition to the detection of the grid pattern according to the first and second embodiments.

Figure 34:
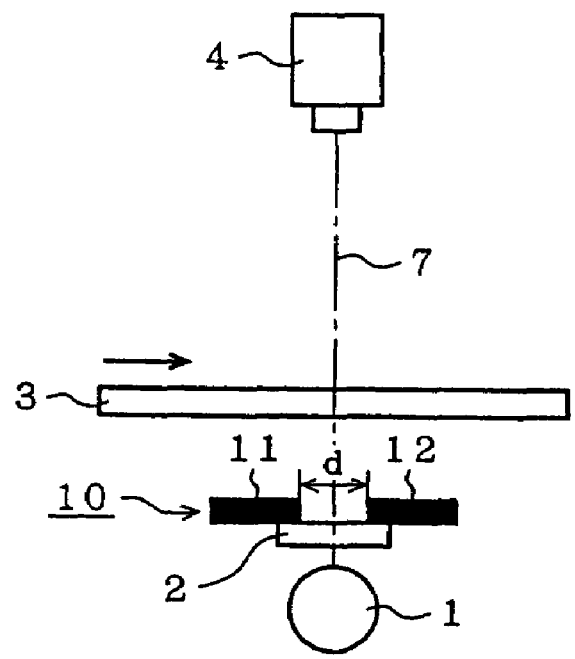
FIG. 34 is a side view schematically explaining the structure of an inspection apparatus according to a third embodiment of the present invention.

FIG. 34 is a schematic side-view for explaining the structure of an inspection apparatus according to the third embodiment of the present invention. Referring to FIG. 34, specifically, the inspection apparatus comprises: the image pickup means 4 that picks-up the image of a plate member 3, as an inspection target; and an illumination 1, and the grid pattern 2 is further arranged between the inspection target 3 and the illumination 1. The conveying direction of the inspection target 3 is shown by an arrow. The image pickup means 4 is arranged, facing the grid pattern 2 and the illumination 1 via the inspection target 3. Further, the inspection apparatus comprises a slit member 10 for improving the detecting sensitivity. The slit member 10 needs to be arranged between the illumination 1 and the image pickup means 4.

Referring to FIG. 34, the slit member 10 comprises a pair of shielding units 11 and 12 and a slit between the pair of shielding units. For example, the slit member 10 is realized by arranging a pair of black shielding plates at a constant interval d.

Figure 35:
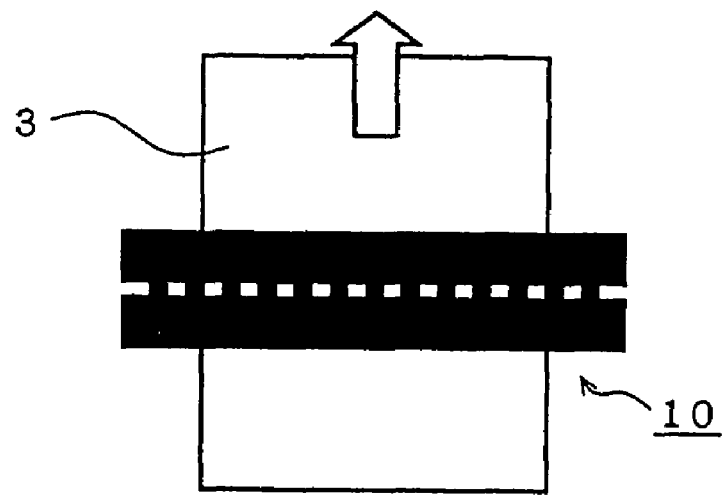
FIG. 35 is a plan view showing an illumination 1 side from the position of image pickup means 4 in the inspection apparatus shown in FIG. 29.

FIG. 35 is a plan view showing the illumination 1 side from the position of the image pickup means 4 in the inspection apparatus shown in FIG. 34. Referring to FIG. 35, the slit member 10 is arranged by matching the longitudinal direction of slit and the array direction of the grid pattern 2. Referring to FIG. 34, an optical axis 7 of the line sensors of the image pickup means 4 is transmitted through the slit. Preferably, the optical axis 7 matches the center of the width direction of slit.

Figure 36:
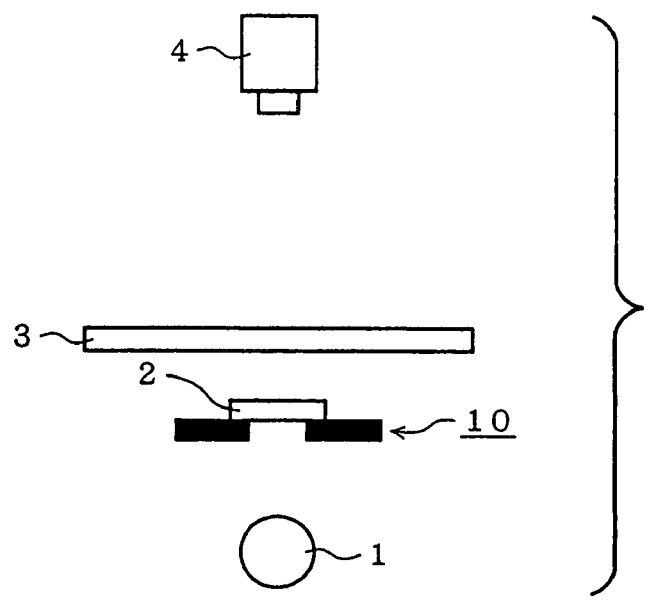
FIG. 36 is a side view schematically explaining one arrangement example of a slit member 10.
Figure 37A:
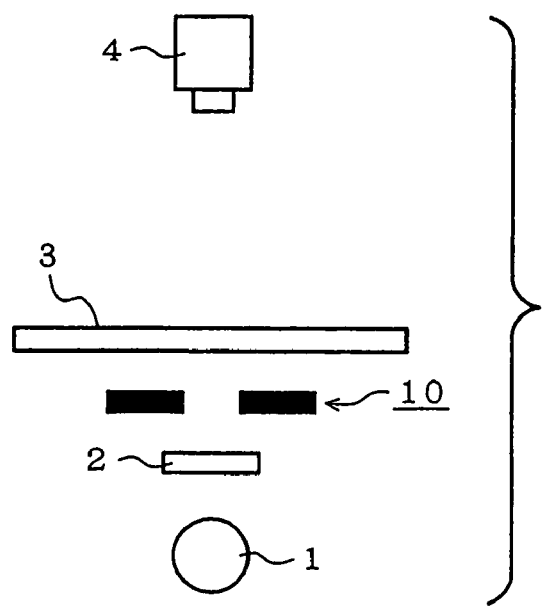
FIG. 37 is a side view schematically explaining another arrangement example of the slit member 10.
Figure 37B:
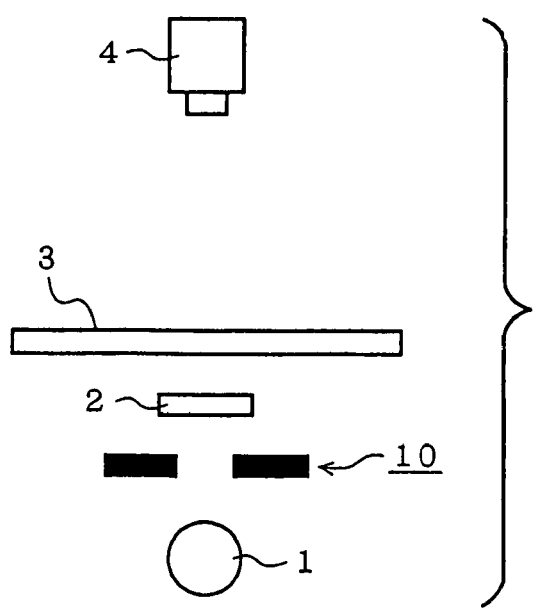
Figure 38:
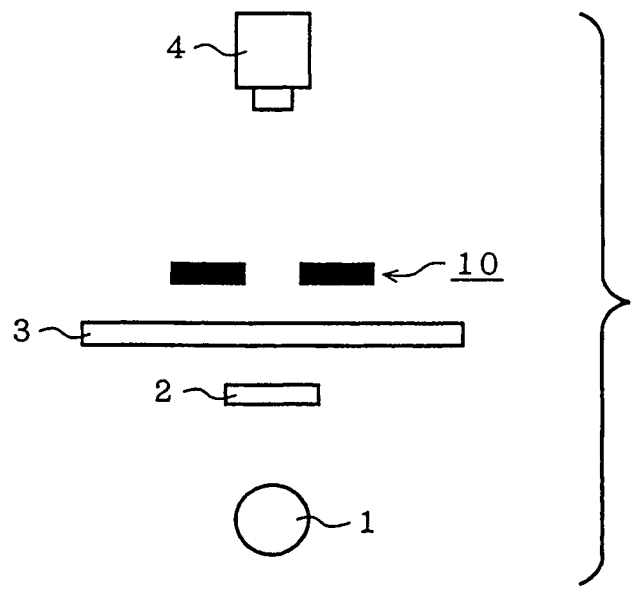
FIG. 38 is a side view schematically explaining another arrangement example of the slit member 10.

FIGS. 36 to 38 are schematic side-views for explaining arrangement examples of the slit member 10. FIG. 34 shows the arrangement example of overlaying the slid member 10 to the top of the grid pattern 2. However, the arrangement of the slit member 10 is not limited to this. According to the present invention, the slit member 10 may be arranged between the illumination 1 and the image pickup means 4. Referring to FIG. 36, the grid pattern 2 may be overlaid to the top of the slit member 10. That is, the slit member 10 may be arranged to the bottom of the grid pattern 2.

Referring to FIGS. 37(A) and 37(B), the slit member 10 may be arranged separately from the grid pattern 2. Further, referring to FIG. 38, the slit member 10 may be arranged to the opposite side of the grid pattern 2, sandwiching the inspection target 3.

Next, a description is given of an improving method of the detecting sensitivity by adjusting the interval d of the slit.

In view of the light diffraction by using the interval d of the slit, a width W of light at the position far from the slit by a length L is the addition of the interval d of the slit and a width Lθ formed by the diffraction (θ: diffraction angle), and is expressed by the following expression.

$$W=d+L\theta \approx d+\lambda L/d (\lambda: \text{light wavelength}) \quad \text{(Expression 21)}$$

In this case, the width W is minimum when the interval d is equal to $\sqrt{(\lambda \cdot L)}$. Then, the width W is equal to $\sqrt{(\lambda \cdot L)}$.

Preferably, the interval d of the slit is arranged to satisfy a relation of d≈$\sqrt{(\lambda \cdot L)}$ (where reference symbol λ is a light wavelength of illumination and reference symbol L is a length from the camera to the slit).

As mentioned above, the expansion of beams from the illumination is suppressed by using the slit at the interval of slit, which is properly set. Further, the inspection is realized with relatively parallel light. Thus, the detecting sensitivity is improved by shielding the stray light.

Third Embodiment

A description is given of the same inspection apparatus as that shown in FIG. 34 according to the third embodiment. The inspection apparatus comprises: an illuminator 1; a CCD camera 4; the grid pattern 2; and the slit member 10, and inspects the refractive power of the optical distortion generated by the defect existing on the inspected member 3 by catching the change in grid patterns.

Specifically, according to the third embodiment, the influence on the refractive power from the optical distortion is inspected in the case of changing the interval d of the slit by using the above-mentioned detecting apparatus of the defect.

A float glass plate with thickness of 1 mm, serving as the inspected member 3, is irradiated with light from the illuminator 1 thereunder, and an image of the glass plate is captured by the CCD camera 4. The illuminator 1 comprises a strip-light that is arranged separated from the rear surface of the glass plate at a predetermined distance for transmission-type illumination. Further, arranged between the glass plate 3 and the illuminator 1 are the grid pattern 2 for detecting the optical distortion generated by the defect existing on the glass plate 3 and the slit member 10 for setting the beams from the illuminator 1 to be parallel and for shielding the stray light. The slit member 10 is arranged for inspection at the interval d of the slit of the slit member 10, ranging d1 to d5. Then, the distance from the CCD camera 4 to the slit member 10 is 1000 mm, and the illumination light is green light (with the wavelength of about 500 nm) or white light.

The image captured by the CCD camera 4 is subjected to image processing by an image processing device. The plurality of types of sine waves deviated in phase at the angle of 90° are calculated based on image data captured by the CCD camera 4 as a result of the image processing, the phase angle at the pixel is obtained based on the plurality of types of sine waves, and the refractive power of the optical distortion is calculated based on the difference in phase angle between the pixels.

Figure 39:
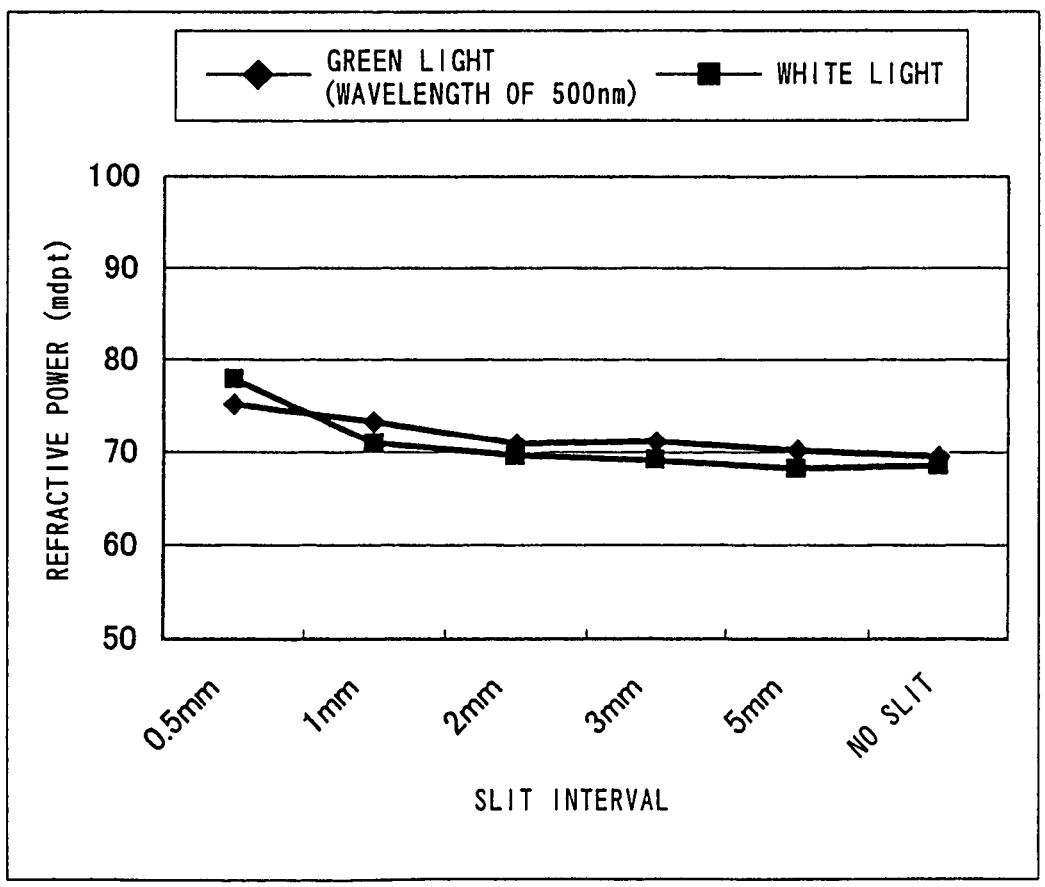
FIG. 39 is a graph showing the influence of a slit with refractive power due to the optical distortion.

A result according to the third embodiment is shown in FIG. 39. FIG. 39 is a graph showing the influence from the slit using the refractive power of the optical distortion according to the third embodiment. Referring to FIG. 39, the refractive power of the optical distortion calculated by the image processing device is expressed by 256 gradations. The abscissa indicates the interval of the slit and the ordinate indicates the refractive power of the distortion (unit: mdpt, millidiopter). The interval of the slit is 0.5 mm, 1 mm, 2 mm, 3 mm, and 5 mm, corresponding to d1 to d5.

As a result shown in FIG. 39, obviously, the refractive power of the optical distortion varies depending on the difference in intervals of the slit. Thus, it is confirmed that the use of slit influences on the refractive power of the optical distortion. As a consequence, it is most advantageous that the interval of slit is 0.5 mm.

As a consequence, obviously, as the interval of slit is narrower, the stray light is shielded and the refractive power of distortion is clearly detected.

In view of the light diffraction by using the interval d of the slit, the width W of light at the position far from the slit by the length L is the addition of the width d of slit and the width $L\theta$ formed by the diffraction, and is expressed by the expression of $W = d + L\theta \approx d + \lambda L/d$ (where reference symbol $\lambda$ denotes a light wavelength). In this case, the width W is minimum when the interval d is equal to $\sqrt{(\lambda \cdot L)}$. Then, the width W is equal to $\sqrt{(\lambda \cdot L)}$. The best width of slit is calculated based on the expression according to the third embodiment and, then, a relation of $W \approx 0.7$ mm in the case of green light.

Therefore, preferably, the interval of slit is set to be approximate to the width calculated by the above-described expression. However, the field of view and the setting situation of the CCD camera must be considered. For example, it must be considered that the interval does not influence the field of view of the CCD camera. Therefore, preferably, such a condition is set that the interval d of slit is 100 μm or more.

Fourth Embodiment

A description is given of the structure using the slit member in addition to the grid pattern according to the third embodiment. In place of the addition of the slit to the grid pattern, the grid width may be narrowed in advance, and the portion other than the grid is masked like a slit with black, thereby forming and using the grid pattern.

Figure 40:
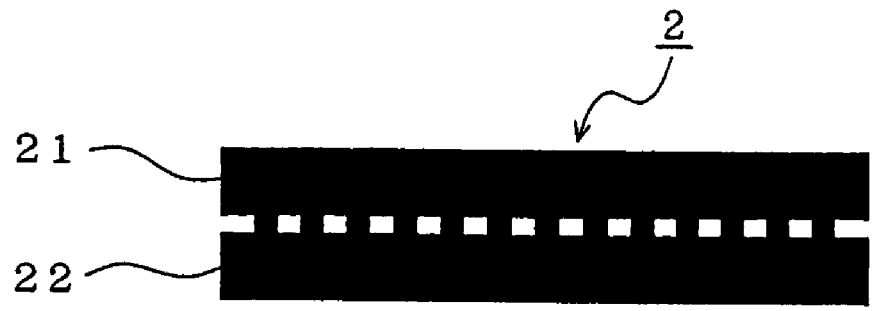
FIG. 40 is a plan view schematically showing a grid pattern according to a fourth embodiment.

FIG. 40 is a schematic plan-view showing the grid pattern according to the fourth embodiment. The grid pattern 2 comprises: a pair of masking units 21 and 22; and a grid arranged between the masking units 21 and 22. The above-mentioned grid pattern 2 is realized by arranging the pair of the masking units 21 and 22 so as to sandwich the grid in the width direction of grid perpendicular to the array direction (longitudinal direction) of grid.

The interval between the masking units 21 and 22 corresponds to the interval d of slit. Therefore, the interval d of the slit is set to be a proper value, thereby improving the detecting sensitivity.

Fifth Embodiment

Figure 41:
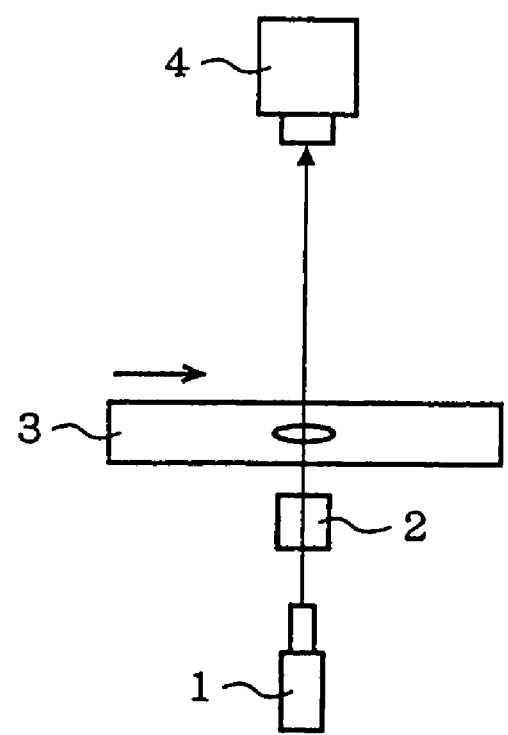
FIG. 41 is a side view schematically explaining the structure of an inspection apparatus according to a fifth embodiment of the present invention.
Figure 42:
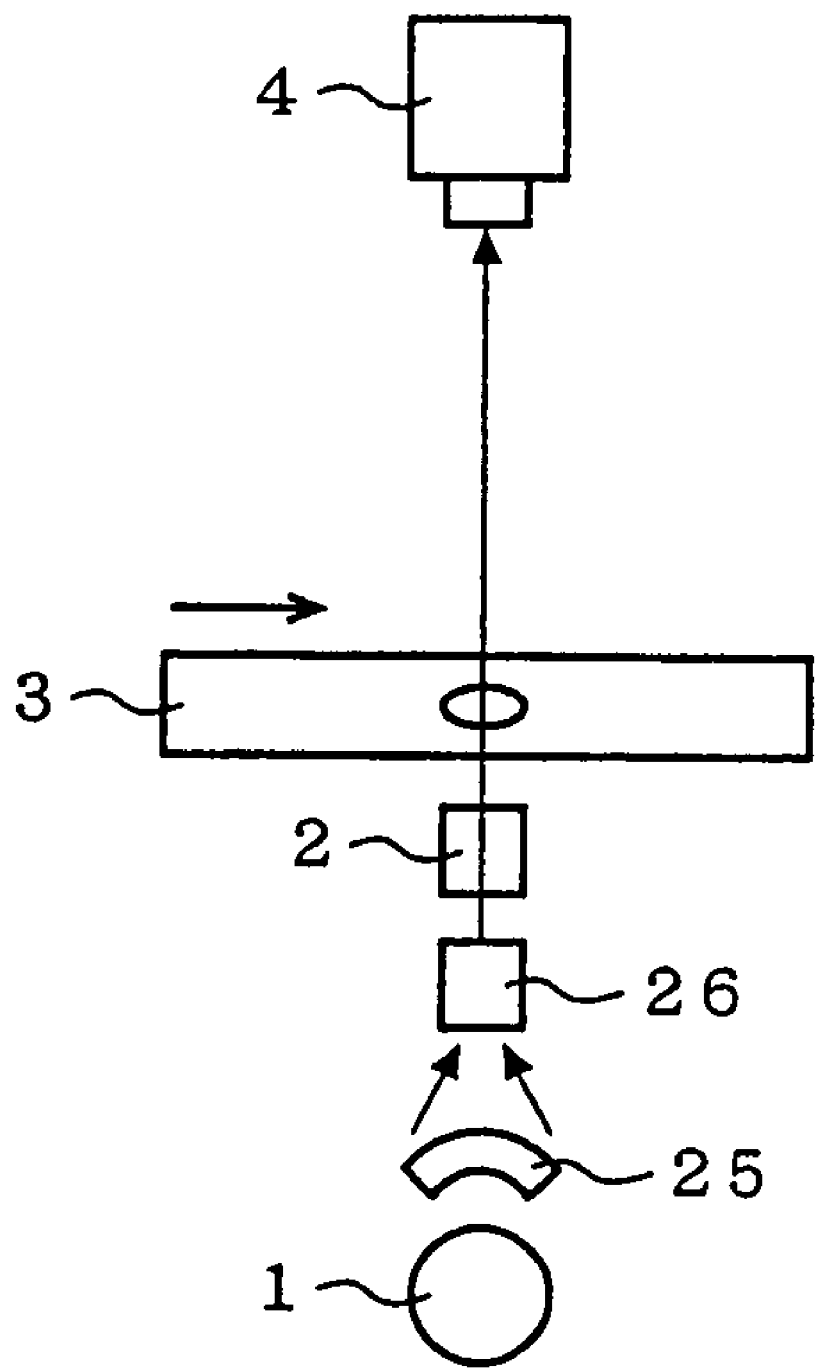
FIG. 42 is a side view schematically explaining the structure of the inspection apparatus according to the fifth embodiment of the present invention.

FIGS. 41 and 42 are schematic side-views for explaining the structure of an inspection apparatus according to the fifth embodiment of the present invention. In place of suppressing the expansion of beams by the slit, a light source for irradiating, like strips, the parallel beams with a narrow width, e.g., laser beams, may be used. Further, a method for narrowing the irradiation width by condensing the illumination light with a lens and for setting the parallel beams may be used.

Specifically, referring to FIG. 41, the laser beams are used, serving as the light source 1. The inspection target 3 may be irradiated, via the grid pattern 2, with stripe parallel beams having the narrow width. Alternatively, referring to FIG. 42, the irradiation width may be narrowed by condensing the illumination light with a condensing lens 25 and the beams may be set to be parallel for irradiation by a collimate lens 26.

Although the present invention is described by using the glass plate, as the inspection target, in the foregoing, the present invention is not limited to this. In addition to the glass plate, the present invention can be applied to another transparent plate member containing resin or glossy plate member.

The transparent plate member, to which the estimating apparatus and the estimating method according to the present invention can be applied, is not limited to a plain plate, and may be a plate with a gentle curvature, such as a panel. Alternatively, the transparent plate member or glossy plate member may be a plate member that is properly cut, or a plate member that is continuously supplied. Further, the estimating apparatus and method can be applied to a semi-transparent plate with transparency.

According to the embodiments, the present invention is described by using the image data captured by the line sensor camera. However, the present invention can be applied to processing of the image data captured by a matrix camera.

INDUSTRIAL APPLICABILITY

As mentioned above, according to the present invention, even in the case of causing the deviation in the regular correspondence between the array pattern of pixels and the image of grid pattern, it is possible to obtain the defect included in the transparent plate member, the refractive power, and the unevenness of surface smoothness of the glossy plate member.

Further, the entire apparatus is structured, as an inexpensive system, because of the omission of precise pitch, minute grid, and telecentric lens.

The invention claimed is:

1. An estimating apparatus of the amount of optical distortion of light transmitted through a transparent plate member with unevenness of refractive power of the transparent plate member, comprising:
   means for irradiating a grid pattern having an array of a bright portion and a dark portion with a constant pitch and a constant width;
   means for picking-up said grid pattern by using an image pickup device including a CCD pixel array;
   means for inputting a signal from said image pickup device, as gray image data;
   means for supporting and conveying said transparent plate member in an optical line ranging from said grid pattern to said image pickup device; and
   image processing means for processing the gray image data inputted from said image pickup device,
   wherein, upon picking-up the image of the grid pattern on said image pickup device, $4n\pm\alpha$ CCD pixels of the CCD pixel array correspond to n grids, where n and $\alpha$ are integers greater than zero and $\alpha$ is less than or equal to n/10, thereby generating a moiré fringes, and
   said image processing means comprises:
   means for calculating a plurality of types of sine waves that are deviated in phase at 90° from image data of said moiré fringes;
   means for obtaining a phase angle at each pixel based on said plurality of types of sine waves; and
   means for calculating refractive power of the optical distortion based on a difference in phase angles between the pixels.

2. An estimating apparatus of the amount of optical distortion of light reflected to a glossy plate member with unevenness of surface smoothness of the plate member, comprising:
   means for irradiating a grid pattern having an array of a bright portion and a dark portion with a constant pitch and a constant width;
   means for picking-up a reflected image of said grid pattern by using an image pickup device including a CCD pixel array;
   means for inputting a signal from said image pickup device, as gray image data;
   means for supporting and conveying the glossy plate member so that light from said grid pattern is reflected to the plate member and is incident on said image pickup device;
   image processing means for processing the gray image data inputted from said image pickup device;
   wherein, upon picking-up the image of the grid pattern on said image pickup device, $4n\pm\alpha$ CCD pixels of the CCD pixel array correspond to n grids, where n and $\alpha$ are integers greater than zero and $\alpha$ is less than or equal to n/10, thereby generating a moiré fringes, and
   said image processing means comprises:
   means for calculating a plurality of types of sine waves that are deviated in phase at 90° from image data on said moiré fringes;
   means for obtaining a phase angle at each pixel based on said plurality of types of sine waves; and
   means for calculating the amount of deviation of the reflected light based on the difference in phase angles between the pixels.

3. An estimating method of the amount of optical distortion of light transmitted through a transparent plate member with unevenness of refractive power of the transparent plate member, comprising:
   a step of pick-up an image of a grid pattern having an array having a bright portion and a dark portion with a constant pitch and a constant width by using an image pickup device including a CCD pixel array and enabling $4n\pm\alpha$ CCD pixels correspond to n grids, where n and $\alpha$ are integers greater than zero and $\alpha$ is less than or equal to n/10, thereby generating a moiré fringes, upon pick-up the image of the grid pattern on said image pickup device, and
   a step of processing, by image processing means, gray image data of the grid pattern picked-up by said image pickup device via said transparent plate number.
   Wherein said step of processing by the image processing means comprises:
   a step of calculating a plurality of types of sine waves that are deviated in phase at 90° from image data on said moiré fringes;
   a step of obtaining a phase angle at each pixel based on said plurality of types of sine waves; and
   a step of calculating refractive power of the optical distortion based on the difference in phase angles between the pixels.

4. An estimating method of the amount of optical distortion of light reflected to a glossy plate member with unevenness of surface smoothness of the plate member, comprising:
   a step of picking-up an image reflected, on the glossy plate member, of a grid pattern having an array having a bright portion and a dark portion with a constant pitch and a constant width by using an image pickup device including a CCD pixel array and enabling $4n\pm\alpha$ CCD, pixels of the CCD pixel array to correspond to n grids, where n and $\alpha$ are integers greater than zero and $\alpha$ is less than or equal to n/10, thereby generating a moiré fringes, upon picking-up the image of the grid pattern on said image pickup device, and
   a step of processing, by image processing means, gray image data of the reflected image of the grid pattern picked-up by said image pickup device,
   wherein said step of processing by the image processing means comprises:
   a step of calculating a plurality of types of sine waves that are deviated in phase at 90° from image data of said moiré fringes;
   a step of obtaining a phase angle at each pixel based on said plurality of types of sine waves; and
   a step of calculating the amount of deviation of the reflected light based on the difference in phase angles between the pixels.

5. A detecting apparatus of a defect having the optical distortion of a transparent plate member, comprising:
- means for irradiating a grid pattern having an array of a bright portion and a dark portion with a constant pitch and a constant width;
- means for picking-up the grid pattern by using an image pickup device including a CCD pixel array;
- means for inputting a signal from said image pickup device, as gray image data;
- means for supporting and conveying the transparent plate member in an optical path ranging from the grid pattern to said image pickup device; and
- image processing means for processing the gray image data inputted from said image pickup device,
  - wherein a moiré fringes are generated by the correspondence of $4n\pm\alpha$ CCD pixels of the CCD pixel array to n grids upon picking-up the grid pattern to said image pickup device, where n and $\alpha$ are integers greater than zero and $\alpha$ is less than or equal to n/10, and
- said image processing means comprises:
- means for calculating a plurality of types sine waves that are deviated in phase at 90° from image data of said moiré fringes;
- means for obtaining a phase angle at each pixel from the plurality of types of sine waves; and
- means for detecting the defect having the optical distortion based on the difference in phase angle between the pixels.

6. A detecting apparatus of a defect having the optical distortion of a surface of a glossy plate member, comprising:
- means for irradiating a grid pattern with an array of a bright portion and a dark portion with a constant pitch and a constant width;
- means for picking-up a reflected image of the grid pattern by using an image pickup device including a CCD pixel array;
- means for inputting a signal from said image pickup device, as gray image data;
- means for supporting and conveying the plate member so that light from the grid pattern is reflected to the glossy plate member and is incident on said image pickup device; and
- image pickup means for processing the gray image data inputted from said image pickup device,
  - wherein a moiré fringes are generated by the correspondence of $4n\pm\alpha$ CCD pixels of the CCD pixel array to n grids upon picking-up the grid pattern to said image pickup device, where n and $\alpha$ are integers greater than zero and $\alpha$ is less than or equal to n/10, and
- said image processing means comprises:
- means for calculating a plurality of types sine waves that are deviated in phase at 90° from image data of said moiré fringes;
- means for obtaining a phase angle at each pixel from the plurality of types of sine waves; and
- means for detecting the defect having the optical distortion based on the difference in phase angle between the pixels.

7. A detecting method of a defect having the optical distortion of a transparent plate member, comprising:
- a step of picking-up, using a CCD pixel array, an image of a grid pattern having an array having a bright portion and a dark portion with a constant pitch and a constant width and generating α moiré fringes by the correspondence of $4n\pm\alpha$ CCD pixels of the CCD pixel array to n grids, where n and $\alpha$ are integers greater than zero and $\alpha$ is less than or equal to n/10, upon picking-up the image of the grid pattern on said image pickup device; and
- a step of processing, by image processing means, gray image data of the grid pattern picked-up by said image pickup device via the transparent plate member,
- wherein said step of processing by the image processing means comprises:
- a step of calculating a plurality of types of sine waves that are deviated in phase at 90° from image data of said moiré fringes;
- a step of obtaining a phase angle at each pixel based on said plurality of types of sine waves; and
- a step of detecting the defect having the optical distortion based on the difference in phase angles between the pixels.

8. A detecting method of a defect having the optical distortion of a surface of a glossy plate member, comprising:
- a step of picking-up, using an image pickup device including an CCD pixel array, an image reflected, on the glossy plate member, of a grid pattern having an array of a bright portion and a dark portion with a constant pitch and a constant width and generating a moiré fringes by the correspondence of $4n\pm\alpha$ CCD pixels of the CCD pixel array to n grids, upon picking-up the reflected image of the grid pattern on said image pickup device, where n and $\alpha$ are integers greater than zero and $\alpha$ is less than or equal to n/10; and
- a step of processing, by image processing means, gray image data of the reflected image of the grid pattern picked-up by said image pickup device,
- wherein said step of processing by said image processing means comprises:
- a step of calculating a plurality of types of sine waves that are deviated in phase by 90° from image data of said moiré fringes;
- a step of obtaining a phase angle at each pixel based on said plurality of types of sine waves; and
- a step of detecting the defect having the optical distortion based on the difference in phase angle between the pixels.

* * * * *

UNITED STATES PATENT AND TRADEMARK OFFICE
CERTIFICATE OF CORRECTION

PATENT NO. : 7,495,760 B2
APPLICATION NO. : 10/540785
DATED : February 24, 2009
INVENTOR(S) : Atsushi Miyake, Yuki Yoshimura and Kunihiro Hiraoka It is certified that error appears in the above-identified patent and that said Letters Patent is hereby corrected as shown below:

Col. 28, Claim 3, line 29 after the word number "." should be --;--.

Col. 28, Claim 3, line 30 "Wherein" should read --wherein--.

Signed and Sealed this

Twenty-eighth Day of April, 2009

JOHN DOLL
*Acting Director of the United States Patent and Trademark Office*